United States Patent [19]

Matheson

[11] Patent Number: 5,848,594
[45] Date of Patent: Dec. 15, 1998

[54] EVALUATING THE WORK CAPACITY OF INJURED PEOPLE

[76] Inventor: Leonard N. Matheson, 31801 Via Perdiz, Trabucco Canyon, Calif. 92679

[21] Appl. No.: 482,234

[22] Filed: Jun. 7, 1995

Related U.S. Application Data

[63] Continuation-in-part of Ser. No. 108,214, Aug. 16, 1993, abandoned, and Ser. No. 252,676, Jun. 2, 1994, abandoned.

[51] Int. Cl.$^6$ .................................................. A61B 19/00
[52] U.S. Cl. .......................... 128/898; 128/898; 600/587
[58] Field of Search ............................. 128/897–98, 696, 128/706, 707, 774; 600/509, 519, 520, 587

[56] References Cited

U.S. PATENT DOCUMENTS

| 4,367,752 | 1/1983 | Jimenez et al. | 128/706 |
|---|---|---|---|
| 4,883,063 | 11/1989 | Bernard et al. | 128/706 |
| 5,243,993 | 9/1993 | Alexander et al. | 128/706 |

OTHER PUBLICATIONS

Alpert, Matheson, Beam, and Mooney, *J. Occup. Rehab.* 1(1);13–30 (1991).
Caldwell, Chaffin, Dukes–Dobos, Kroemer, Laubauch, Snook, and Wasserman Am. Ind. *Hyg. Assoc. J.* Apr. 201–206 (1974).
Chaffin, *Am. Ind. Hyg. Assoc. J.* 36;505–511 (1975).
Chaffin, Herrin, and Keyserling, *J. Occup. Med.* 20(6);403–408 (1978).
Garg, Mital, and Asfour, *Ergonomics* 23(1);13–27 (1980).
Karwowski, *Ergonomics* 34(4);487–496 (1991).
Khalil, Waly, Genaidy, and Asfour, *Am. Ind. Hyg. Assoc. J.* 48(12);951–956 (1987).
Kishino, Mayer, Gatchel, Parrish, Anderson, Gustin and Mooney, *Spine* 10(10);921–927 (1985).
Kroemer, *Human Factors* 25(5);493–506 (1983).
Matheson, *EPIC Lift Capacity Evaluation Manual* (1992).
Matheson, *EPIC Lift Capacity Evaluation Manual* (1993).
Matheson, Danner, Grant, and Mooney, *J. of Occupational Rehab* . 3(2);65–81 (1993).
Matheson, Mooney, Grant, Affleck, Hall, Melles, Lichter, and McIntosh, *Spine* 20(19);2119–2129 (1995).
Matheson, Mooney, Holmes, Leggett, Grant, Negri, and Holmes, *Spine* 20(19);2130–2134 (1995).
Mayer, Barnes, Nichols, Coval, Piel, Hoshino, and Gatchel, *Spine* 13(9);993–997 (1988).
Mayer, Barnes, Kishino, Nichols, Gatchel, Mayer, and Mooney, *Spine* 13(9);998–1002 (1988).
Mital, *Human Factors* 25(5);485–491 (1983).
Ogden–Niemeyer, *Procedure Guidelines for the West Standard Evaluation* (1989,1991).
Pytell and Kamon, *Ergonomics* 24(9);663–672 (1981).
Snook, *Ergonomics* 28(1);327–330 (1985).
Snook, *Ergonomics* 28(1);331–333 (1985).

*Primary Examiner*—John P. Lacyk
*Attorney, Agent, or Firm*—Weil, Gotshal & Manges LLP

[57] ABSTRACT

Methods are provided for evaluating the physical work capacity of a person by determining maximum acceptable lifting weight. The methods may also provide a normative performance ranking, may monitor starting heart rate as an indicia of maximum acceptable weight, and may use a progressive or recursive set of subtests. The invention further includes methods for evaluating constant work capacity, and also includes devices and kits for practicing the claimed methods.

23 Claims, 19 Drawing Sheets

| Normal Healthy Female Maximum Acceptable Weight |||||||
|---|---|---|---|---|---|---|
| Percentile | Test #1 | Test #2 | Test #3 | Test #4 | Test #5 | Test #6 | Percentile |
| 90th | 60 | 80 | 55 | 45 | 60 | 50 | 90th |
| 85th | 57 | 73 | 52 | 43 | 57 | 48 | 85th |
| 80th | 53 | 67 | 48 | 42 | 53 | 47 | 80th |
| 75th | 50 | 60 | 45 | 40 | 50 | 45 | 75th |
| 70th | 47 | 57 | 43 | 38 | 47 | 38 | 70th |
| 65th | 43 | 53 | 42 | 37 | 43 | 35 | 65th |
| 60th | 43 | 53 | 41 | 36 | 43 | 34 | 60th |
| 55th | 42 | 52 | 41 | 36 | 42 | 33 | 55th |
| 50th | 40 | 50 | 40 | 35 | 40 | 30 | 50th |
| 45th | 37 | 47 | 37 | 32 | 37 | 27 | 45th |
| 40th | 33 | 43 | 33 | 28 | 33 | 23 | 40th |
| 35th | 33 | 43 | 33 | 28 | 33 | 23 | 35th |
| 30th | 32 | 42 | 32 | 27 | 32 | 22 | 30th |
| 25th | 30 | 40 | 30 | 25 | 30 | 20 | 25th |
| 20th | 27 | 37 | 28 | 23 | 28 | 18 | 20th |
| 15th | 23 | 33 | 27 | 22 | 27 | 17 | 15th |
| 10th | 20 | 30 | 25 | 20 | 25 | 15 | 10th |

FIG.4a

| Normal Healthy Female Relative Acceptable Weight |||||||
|---|---|---|---|---|---|---|
| Percentile | Test #1 | Test #2 | Test #3 | Test #4 | Test #5 | Test #6 | Percentile |
| 90th | .429 | .570 | .513 | .383 | .509 | .458 | 90th |
| 85th | .410 | .547 | .489 | .366 | .489 | .437 | 85th |
| 80th | .392 | .525 | .466 | .350 | .468 | .415 | 80th |
| 75th | .373 | .502 | .442 | .333 | .448 | .394 | 75th |
| 70th | .341 | .465 | .401 | .305 | .415 | .358 | 70th |
| 65th | .310 | .427 | .361 | .276 | .381 | .321 | 65th |
| 60th | .302 | .418 | .351 | .269 | .373 | .312 | 60th |
| 55th | .297 | .412 | .344 | .265 | .368 | .307 | 55th |
| 50th | .278 | .390 | .320 | .248 | .348 | .285 | 50th |
| 45th | .261 | .353 | .292 | .233 | .315 | .260 | 45th |
| 40th | .244 | .315 | .264 | .218 | .281 | .236 | 40th |
| 35th | .240 | .306 | .257 | .214 | .273 | .230 | 35th |
| 30th | .237 | .300 | .253 | .212 | .268 | .226 | 30th |
| 25th | .227 | .278 | .236 | .203 | .248 | .211 | 25th |
| 20th | .216 | .267 | .224 | .193 | .238 | .200 | 20th |
| 15th | .206 | .255 | .212 | .184 | .228 | .190 | 15th |
| 10th | .195 | .244 | .200 | .174 | .218 | .179 | 10th |

FIG.4b

| Normal Healthy Male Maximum Acceptable Weight ||||||||
|---|---|---|---|---|---|---|---|
| Percentile | Test #1 | Test #2 | Test #3 | Test #4 | Test #5 | Test #6 | Percentile |
| 90th | 90 | 105 | 95 | 80 | 90 | 80 | 90th |
| 85th | 88 | 103 | 93 | 77 | 87 | 77 | 85th |
| 80th | 87 | 102 | 92 | 73 | 83 | 73 | 80th |
| 75th | 85 | 100 | 90 | 70 | 80 | 70 | 75th |
| 70th | 80 | 95 | 83 | 65 | 73 | 60 | 70th |
| 65th | 75 | 90 | 77 | 60 | 67 | 57 | 65th |
| 60th | 74 | 89 | 75 | 59 | 65 | 55 | 60th |
| 55th | 73 | 88 | 74 | 58 | 64 | 54 | 55th |
| 50th | 70 | 85 | 70 | 55 | 60 | 50 | 50th |
| 45th | 63 | 77 | 65 | 52 | 57 | 48 | 45th |
| 40th | 57 | 68 | 60 | 48 | 53 | 47 | 40th |
| 35th | 55 | 66 | 59 | 48 | 53 | 46 | 35th |
| 30th | 54 | 65 | 58 | 47 | 52 | 46 | 30th |
| 25th | 50 | 60 | 55 | 45 | 50 | 45 | 25th |
| 20th | 43 | 53 | 50 | 38 | 45 | 38 | 20th |
| 15th | 37 | 47 | 45 | 32 | 40 | 32 | 15th |
| 10th | 30 | 40 | 40 | 25 | 35 | 25 | 10th |

FIG.5a

| Normal Healthy Male Relative Acceptable Weight ||||||||
|---|---|---|---|---|---|---|---|
| Percentile | Test #1 | Test #2 | Test #3 | Test #4 | Test #5 | Test #6 | Percentile |
| 90th | .526 | .643 | .557 | .452 | .500 | .457 | 90th |
| 85th | .504 | .620 | .541 | .432 | .487 | .425 | 85th |
| 80th | .483 | .597 | .526 | .413 | .473 | .392 | 80th |
| 75th | .461 | .574 | .510 | .393 | .460 | .360 | 75th |
| 70th | .439 | .536 | .475 | .373 | .438 | .347 | 70th |
| 65th | .416 | .499 | .441 | .353 | .416 | .334 | 65th |
| 60th | .411 | .489 | .432 | .348 | .411 | .331 | 60th |
| 55th | .407 | .484 | .427 | .345 | .407 | .329 | 55th |
| 50th | .394 | .461 | .406 | .333 | .394 | .321 | 50th |
| 45th | .374 | .432 | .378 | .310 | .361 | .300 | 45th |
| 40th | .355 | .403 | .350 | .288 | .327 | .278 | 40th |
| 35th | .350 | .396 | .343 | .282 | .319 | .273 | 35th |
| 30th | .347 | .391 | .339 | .279 | .314 | .270 | 30th |
| 25th | .335 | .374 | .322 | .265 | .294 | .257 | 25th |
| 20th | .295 | .327 | .283 | .239 | .262 | .229 | 20th |
| 15th | .256 | .281 | .245 | .214 | .230 | .200 | 15th |
| 10th | .216 | .234 | .206 | .188 | .198 | .172 | 10th |

FIG.5b

| MTM Percent | 2 Hours | One Hour | 15 Minutes | 1 Minute | MTM Percent |
|---|---|---|---|---|---|
| 150% | 597 | 298 | 75 | 5 | 150% |
| 140% | 557 | 278 | 70 | 5 | 140% |
| 130% | 517 | 259 | 65 | 4 | 130% |
| 120% | 477 | 239 | 60 | 4 | 120% |
| 110% | 438 | 219 | 55 | 4 | 110% |
| 100% | 398 | 199 | 50 | 3 | 100% |
| 90% | 358 | 179 | 45 | 3 | 90% |
| 80% | 318 | 159 | 40 | 3 | 80% |
| 70% | 278 | 139 | 35 | 2 | 70% |
| 60% | 239 | 119 | 30 | 2 | 60% |
| 50% | 199 | 99 | 25 | 2 | 50% |

FIG.6a

| MTM Percent | 2 Hours | One Hour | 15 Minutes | 1 Minute | MTM Percent |
|---|---|---|---|---|---|
| 150% | 584 | 292 | 73 | 5 | 150% |
| 140% | 545 | 272 | 68 | 5 | 140% |
| 130% | 506 | 253 | 63 | 4 | 130% |
| 120% | 467 | 234 | 58 | 4 | 120% |
| 110% | 428 | 214 | 54 | 4 | 110% |
| 100% | 389 | 195 | 49 | 3 | 100% |
| 90% | 350 | 175 | 44 | 3 | 90% |
| 80% | 311 | 156 | 39 | 3 | 80% |
| 70% | 272 | 136 | 34 | 2 | 70% |
| 60% | 234 | 117 | 29 | 2 | 60% |
| 50% | 195 | 97 | 24 | 2 | 50% |

FIG.6b

| MTM Percent | 2 Hours | One Hour | 15 Minutes | 1 Minute | MTM Percent |
|---|---|---|---|---|---|
| 150% | 597 | 298 | 75 | 5 | 150% |
| 140% | 557 | 278 | 70 | 5 | 140% |
| 130% | 517 | 259 | 65 | 4 | 130% |
| 120% | 477 | 239 | 60 | 4 | 120% |
| 110% | 438 | 219 | 55 | 4 | 110% |
| 100% | 398 | 199 | 50 | 3 | 100% |
| 90% | 358 | 179 | 45 | 3 | 90% |
| 80% | 318 | 159 | 40 | 3 | 80% |
| 70% | 278 | 139 | 35 | 2 | 70% |
| 60% | 239 | 119 | 30 | 2 | 60% |
| 50% | 199 | 99 | 25 | 2 | 50% |

FIG.13a

| MTM Percent | 2 Hours | One Hour | 15 Minutes | 1 Minute | MTM Percent |
|---|---|---|---|---|---|
| 150% | 584 | 292 | 73 | 5 | 150% |
| 140% | 545 | 272 | 68 | 5 | 140% |
| 130% | 506 | 253 | 63 | 4 | 130% |
| 120% | 467 | 234 | 58 | 4 | 120% |
| 110% | 428 | 214 | 54 | 4 | 110% |
| 100% | 389 | 195 | 49 | 3 | 100% |
| 90% | 350 | 175 | 44 | 3 | 90% |
| 80% | 311 | 156 | 39 | 3 | 80% |
| 70% | 272 | 136 | 34 | 2 | 70% |
| 60% | 234 | 117 | 29 | 2 | 60% |
| 50% | 195 | 97 | 24 | 2 | 50% |

FIG.13b

How much does this weigh?

1................Like nothing at all
2................Very light
3................Light
4................Light-Medium
5................Medium
6................Medium-Heavy
7................Heavy
8................Very heavy
9................Extremely heavy
10..............Too heavy

FIG.14

EVALUATING THE WORK CAPACITY OF INJURED PEOPLE

CROSS-REFERENCE TO RELATED APPLICATIONS

This application is a continuation-in-part of U.S. patent application Ser. No. 08/108,214 filed on Aug. 16, 1993, now abandoned, and is also a continuation-in-part of U.S. patent application Ser. No. 08/252,676 filed on Jun. 2, 1994, now abandoned, which disclosures are hereby incorporated by reference.

INTRODUCTION

1. Field of Invention

This invention relates to the evaluation of the lifting work capacity and constant work capacity of persons, and particularly of older, injured or disabled persons.

2. Background

In today's world a number of situations arise where an evaluation needs to be made of the capacity of a person to do work. Such an evaluation is often pertinent in situations where a person previously has been injured, has recovered from such injuries and now wishes to return to the work place or where a person is an older worker. In such instances, it is not only important to know what type of work that person can do but also how much of the work that person could be capable of doing if the person receives the correct remedial or conditioning treatment.

In general, the work capacity of a person can be evaluated in terms of three coincidental domains of function:

1. The biomechanical domain which relates to the physical demands placed on the person by the work task and which challenge the persons musculoskeletal system;
2. The psychophysical domain which relates to the demands placed on a person by the work task and which challenge the person's self perceptions, fears and built in work function limits; and
3. The cardiovascular/metabolic domain which relates to the demands placed on the person by the work task and which challenge the cardiac, respiratory and metabolic system of the person.

Accordingly, any procedure for evaluating the work capacity of a person should recognize these three domains and in some way deal with each.

In addition, such evaluation procedure should always be safe, reliable, valid, practical and useful. Briefly speaking, safety relates to limiting the exposure of the person being evaluated to an undue risk of injury; reliability relates to the degree to which the person being evaluated has a consistent performance over time and to the degree to which the evaluation is consistent across different evaluators; validity is the extent to which the measure of the person's performance is related to some objective and true criteria; practicality relates to the ease of administration of a test and utility relates to the applicability of the findings to the real problem on hand.

There are three general methods of strength testing which are used. They can be differentiated in terms of the effect of the test on muscular contraction. These are isometric, isokinetic and isoinertial. In isometric testing, the muscle length is maintained in a static position under load. Force is measured in one biomechanical position. In isokinetic testing, the muscle lengthens or shortens at a fixed rate as a consequence of external control of the velocity of movement of the biomechanical unit. Force is measured throughout the range of movement. In isoinertial testing, the muscle shortens in response to a constant external force. As the biomechanical geometry changes to accomplish movement, changes in muscle length occur at varying velocities. Force is inferred from the mass that is moved.

A large number of tests have been developed over the years which use these methods in an attempt to quantify accurately the work capacity of a person who has been injured or disabled and which to some degree meet the above criteria. However, none of the previously developed tests adequately both meets the above criteria with regard to the evaluation of e.g., lift capacity and constant work capacity, and is also cheap and efficient to administer.

The need, therefore, still exists for a method of testing the lifting work capacity of a person which is safe, reliable, produces a valid result, is practical, cheap and efficient to administer and has demonstrated utility.

RELEVANT LITERATURE

References relating to the use of isometric, isokinetic and isoinertial testing include the following. As to isometric strength testing, Garg, Mital, and Asfour (1980) *Ergonomics* 23(1):13–27; Chaffin (1975) *Am. Ind. Hyg. Assoc. J.* 36:505–510; and Caldwell, Chaffin, Dukes-Dobos, and Kroemer (1974) *Am. Ind. Hyg. Assoc. J.* April: 201–206 have reported that isometric strength tests are safe. On the other hand, Kishino, Mayer, Gatchel, Parrish, Anderson, Gustin and Mooney (1985) *Spine* 10(10):921–927, reported that most incidents of muscle strain or prolonged soreness occurred as a consequence of isometric testing. See also, Battie, Bigos, Fisher, and Hanson (1986), and Zeh, Hanson, Bigos, Spengler, Battie, and Wortley (1987). Marras, King, and Joynt (1984) discuss differences in EMG activity resulting from isometric versus isokinetic tasks.

As to isokinetic testing, it has been found to be reliable in several studies. E. G., Aitkens, Lord, Bernauer, & McCrory (1987); Langrana, Lee, Alexander, & Mayott (1984); McCrory, Aitkens, Avery, & Bernauer (1989); Rose, Delitto & Crandell (1988); Smith, Mayer, Gatchel, & Becker (1985); Alpert, Matheson, Beam, and Mooney (1991) *J. Occup. Rehabilitation* 1(1); Frykman, Harman & Vogel (1988) *Med. Sci. Sports EX.* 20:87; and Porterfield, Mostardi, King, Ariki, Moats, & Noe (1987). However, isokinetic testing has been criticized by Rothstein, Lamb, & Mayhew (1987); Timm (1988); Kishino et al (1985); and Mayer, Barnes, Kishino, Gatchel, Mayer, and Mooney (1988) *Spine* 13(9):993–1002.

As to isoinertial testing, it has been advocated by Snook (1985) *Ergonomics* 28(1):327–333; Garg, Mital, and Asfour (1980) *Ergonomics* 23(1):13–27; Khalil, Waly, Genaidy, and Asfour (1987) *Am. Ind. Hyg. Assoc. J.* 48:951–956; and Pytell and Kamon (1981) *Ergonomics* 24(9):663–672. It has been criticized by Chaffin, Herrin, and Keyserling (1978) *J. Occup. Med.* 20(6):403–408; Mital (1983) *Human Factors* 25(5):485–491; and Karwowski (1991) *Ergonomics* 34:487–496. A progressive lift capacity approach to isoinertial measurement is described by Kroemer (1983) *Human Factors* 25(5):493–506; Matheson (1986) *Vocational Evaluation and Work Adjustment Bulletin* 19(3):107–111; and Mayer et al. (1988) Spine 13(9):993–1002.

SUMMARY OF THE INVENTION

The present invention is directed towards methods for evaluating the lifting work capacity, high risk work factors and vertical range lift capacity of a person, based upon the maximum acceptable weight that the person can lift, and methods for evaluating constant work capacity of a person, based upon the number of times a weight can be lifted within a given time period. Methods for evaluating lifting work capacity include the steps of determining the maximum acceptable weight that the person can lift, obtaining a normative performance ranking based upon that maximum acceptable weight, and using that normative performance ranking to evaluate the lifting capacity of a person. The method for determining the maximal acceptable lifting weight for a person includes the steps of lifting a progressive series of weights until the heart rate of the person does not return between lifts to the starting heart rate, wherein the maximum acceptable lifting weight is the next to the last weight lifted. The method for evaluating the vertical range lift capacity includes the steps of determining a first maximum acceptable weight for a first subtest, performing at least one progressive subtest and determining any corresponding maximum acceptable weight thereof, and evaluating the vertical lift capacity by comparing those maximum acceptable weight values. The method for evaluating the constant work capacity includes the steps of requiring a person to lift a predetermined weight through a predetermined vertical range at a maximal frequency, obtaining a performance ranking based on that frequency, and using that performance ranking to evaluate the constant work capacity of a person. The invention also includes devices for evaluating the lifting capacity of a person using heart rate indicators and lifting limit indicators, and a kit for evaluating lifting capacity comprising an evaluative weight container and a set of masked weights.

The methods, devices and kits of the claimed invention are useful for evaluating the lifting or work capacities of persons who are recovering or have recovered from an injury or illness. The invention is also useful for evaluating older test subjects, in particular for evaluating the capacities of older workers, e.g., workers in the 55–65 year old age range. The invention is particularly useful because it provides safe methods of evaluating persons who might otherwise be at elevated risk of injury or re-injury if tested with other, less preferable testing methods described in the literature. The invention is also useful for evaluating the veracity of an individual's claim that his work capacity has been compromised by injury or illness.

DESCRIPTION OF THE DRAWINGS

In the accompanying drawings:

FIGS. 4(a) and 4(b) are charts used to determine the maximum and relative acceptable weight percentiles for a woman during the diagnostic phase of the procedure of the invention;

FIGS. 5(a) and 5(b) are charts similar to those in FIGS. 5(a) and 5(b) but are used when evaluating men;

FIGS. 6(a) and 6(b) are correlation charts similar to those in FIGS. 5(a) and 5(b) but are use for determining evaluation criteria for amount of weight lifted by an Experimental man.

FIGS. 13(a) and 13(b) are charts illustrating methods-time-measurement (MTM) standards for medium and heavy constant work.

FIG. 14 is a visual index of the rating of perceived load.

DETAILED DESCRIPTION OF THE INVENTION

Figure 1C:
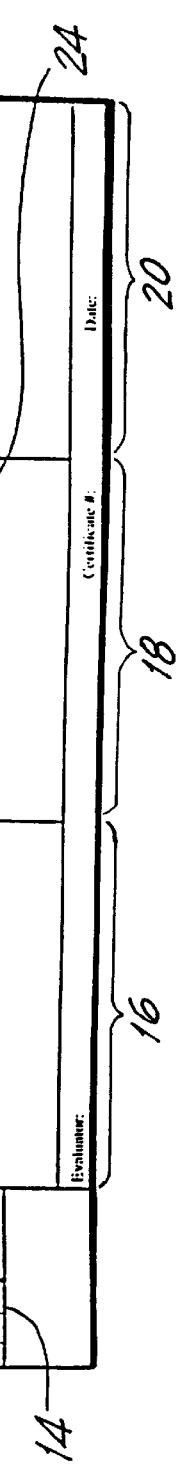
FIGS. 1(a) to (d) are depictions of the front face of four typical evaluation charts for use with the procedure of this invention.

The methods of the claimed invention evaluate aspects of a person's lifting capacity based upon the maximum acceptable weight that can be lifted. The methods are designed to optimize safety, reliability, validity, practicality, efficiency and utility. The methods of the claimed invention feature normative performance rankings, use of the starting heart rate as an indicator of an evaluee's ability to safely progress with the evaluation, and use of a progressive or recursive testing pattern. Some aspects of the claimed invention require the person to lift a predetermined weight a predetermined number of times through a predetermined vertical range, and then to incrementally increase that weight until a safety limit is reached. The heartrate of the person may be monitored between lifts and preferably is monitored throughout the evaluation to ensure that a maximum heart rate is not exceeded. If the evaluee's heart rate returns to the starting heart rate within a predetermined period of time, then the person initiates the next lifting step with an incrementally greater weight. In some preferred embodiments of the methods of the claimed invention, the starting heart rate may be calculated based upon the person's age, and may most preferably be achieved within 120 seconds of the lifting. In other preferred embodiments, the maximum lifting weight may be gender-specific, or more preferably be based upon gender-neutral criteria such as height.

The performance ranking of the claimed invention preferably compares the individual normatively to other individuals, based upon either maximum acceptable weight or relative acceptable weight. The performance rankings are rapid and easy to use by the evaluator, and provide accurate information because the makings are based on normatively distributed data collected from individuals of both genders over several different age ranges. Inter-person reliability of reporting is enhanced by the use of these normative rankings because all individuals are evaluated and ranked with regard to the same, easily quantifiable criteria.

In some preferred embodiments, each weight is lifted more than once, and most preferably four times each, through preselected vertical ranges. The claimed methods preferably provide a series of subtests that are designed to progressively increase the work performed in each lifting motion, both by changing the vertical range of the lift and the frequency of the lifting repetitions for each weight. In some preferred embodiments, subtests having four repetitions begin with a weight that is 40% of the weight used for the corresponding single repetition subtest, and subtests requiring a lift from floor to shoulder level uses a starting weight that is 70% of the weight used during a subtest featuring either a floor to knuckle or knuckle to shoulder lift.

The invention offers several advantages over existing testing methods that are used, including the following. Both cardiovascular and biomechanical safety limits may be incorporated in the test routine, and may be selected based on the evaluator's assessment of the particular area of risk presented by given test subject. This is particularly important in the assessment of motivated older workers whose cariovascular or biomechanical capabilities may be exceeded by their psychological motivation.

As described in detail elsewhere herein, the safety, reliability, validity, practicality, efficiency and utility of the claimed methods can be optimized still further by adding or further defining certain parameters. As an example of optimizing safety, in some preferred embodiments the evaluee is not permitted to exceed safety controls such as (a) starting heart rate, which provides a margin of safety for the evaluee and decreases the likelihood that the maximum heart rate will be achieved during a lifting repetition; (b) maximum heart rate, above which undesirable cardiovascular incidents may occur; and (c) lifting limits addressing common biomechanical limitations. The lifting limits may preferably be based upon gender, height or a target weight.

The safety of the invention may also be optimized in preferred embodiments by evaluating high risk work factors, more preferably stance and horizontal displacement factors, while the person performs the methods of the claimed invention. It is important to monitor such high risk work factors because allowing an evaluee to lift a weight in his or her preferred style often invites injury, particularly in the case of workers that are highly motivated to perform well during the evaluation. Safety also may be optimized by preferred embodiments of the claimed methods that monitor a person's rating of perceived load, pain indicators and body mechanics. Rating of perceived load is an important guideline, because it provides a cognitive limit that is easily understood by the evaluee, and therefore is an important safety factor in deterring overachievers from exceeding biomechanical limits. The rating of perceived load also facilitates inter-evaluee comparisons because it gives each evaluee a common evaluative framework.

Safety is also optimized by the recursive or progressive nature of the subtest series. "Progressive" tests are designed to provide a sequence of subtests in which each subtest is inherently more challenging than the prior test. "Recursive" tests are designed both to provide a sequence of subtests in which each subtest is inherently more challenging than the prior test and to provide lifting weights that are based on the evaluee's lifting performance during the previous subtest. In order to optimize the number of evaluees able to complete a full series of subtests, the increased demands made by full floor-to-shoulder lifts and increased repetitions of lifts could be accommodated by providing decreased weights for the more demanding subtests. Preferred weights are described herein. A recursive series of subtests optimizes safety because evaluees are less likely to exceed musculoskeletal or cardiovascular limits during later tests.

Other aspects of the methods of the claimed invention provide for optimizing validity of the methods of the claimed invention. For example, recursive subtests maximize validity because the weights lifted, and the ultimate maximum weights achieved, reflect the evaluee's lifting capacity rather than fatigue. Such testing regimens thus are distinctly advantageous over testing regimens that emphasize a more kinetic approach—e.g., requiring several repetitions of a lift within a relatively short time period. Validity of the evaluation is further enhanced in preferred embodiments of the invention featuring full-range lifts—e.g., floor-to-shoulder. This is particularly true because a person's capacity for full-range lifts often cannot be accurately extrapolated from lifts over lesser vertical ranges. Also, the methods of the claimed invention provide superior validity because the tests evaluate a longer period of peak force, and through a greater range of motion, than is tested by some evaluation methods in the literature (e.g., isometric). Because the evaluee's lifting is not artificially limited—e.g., by requiring the work to be performed at a fixed speed—the person's muscles and the spine react in a way that more closely simulates realworld lifting and work requirements, and thus the data is a more valid reflection of the subject's capabilities.

Other aspects of the methods of the claimed invention provide for optimizing reliability. For example, preferred embodiments of the invention use masked weights, for example canisters of equal size and shape with color-coded indications of weight that are known by the evaluator but not by the evaluatee. Because the evaluatee does not know the weight being lifted, psychological self-limiting is restricted to the performance parameters imposed by the test. This in turn improves the reliability and validity of the evaluee's rating of perceived load and improves inter-person comparability of the resulting data. Masked weights also advantageously allow an evaluator to determine whether an evaluatee is expending honest effort in the test, by allowing the evaluator to compare the maximum lifting weights achieved during corresponding one repetition and four repetition subtests. Also, masked weights provide enhanced validity because lifters in real-life situations typically do not know the weight of the object lifted and instead respond to their own cardiovascular or biomechanical stimuli in deciding whether the load can be lifted. As another example, reliability is enhanced by providing each evaluatee with a cognitive framework for evaluating the test, e.g., by asking the evaluatee whether the lift could be performed "safely and reliably 8–12 times per day." Also, comparison of data resulting from, for example, one lifting repetition versus four lifting repetitions of the same weight allows an evaluator to gauge the reliability of the lifting test for that subject. Reliability of the methods of the invention may be further enhanced by using the kit provided by the claimed invention, and specifically in using an evaluative weight container that is designed to center and stabilize the lifted weight and/or to provide grips that reduce or eliminate variability due to varying wrist flexibility and strength.

Other aspects of the methods of the claimed invention provide for optimizing efficiency. For example, recursive test series allow an evaluator to start each subsequent subtest at an appropriate weight, and thus may avoid wasting time by requiring an evaluee to lift low weights that do not present a challenge to that evaluee. Efficiency may also be enhanced by monitoring the starting heart rate as an indicator of when to progress with the next lift, in contrast to requiring the evaluatee to wait a predetermined amount of time between each lift that has been selected to provide an adequate safety margin.

The usefulness of the invention is further maximized when embodiments are selected that compare varying vertical ranges and repetitions. Comparison of lifting capacities of different vertical ranges, for example, may provide valuable insight into how efficient or strong some muscle groups are in comparison to other muscle groups that are used for different ranges of motion.

Overview of a Preferred Evaluation Procedure

The EPIC Lift Capacity (ELC) test of this invention has been designed to be a safe, reliable, valid, efficient and practical test of lifting and lowering capacity. The ELC is a battery of six related tests of dynamic lifting and lowering capacity over three vertical ranges with two frequencies of repetition. Primary consideration in the development of the ELC has been given to integrate safety controls so that the safety, of the test battery is optimized. Safety controls and guidelines have been "designed-in" to the ELC test in the areas of equipment and protocol design (order of the tests, starting load, rate of progression of testing, task frequency and range of motion, and other test characteristics), pre-evaluation screening limits (certain people may not be tested safely with the ELC test battery or may require modification of the battery or of the testing circumstances), test performance targets and safety limits (the evaluee's response to the test, the purpose for the testing, performance targets, etc.), and evaluator training and certification.

ELC testing includes the implementation of all of the safety controls and guidelines in these four areas, each of which will be presented separately. It is important for the evaluator to note that a distinction is made between a control and a guideline. A control is an aspect of the test that governs the evaluator's behavior and preferably determines action at a specific point in the test. A guideline is an aspect of the test which preferably should be considered and which, with sufficient rationale, may be exceeded on an individualized case basis. In this description, a control is designated by a "C" while a guideline is designated by a "G" presented in parentheses. Specific procedures which are based on these controls and guidelines are described in detail below.

Equipment and Protocol Design

The ELC has been designed to consider the "action limit" method of manual materials handling risk assessment (NIOSH, 1981) and the safety factors that have been shown to be effective with the WEST Standard Evaluation and Progressive Isoinertial Lifting Evaluation. These factors include:

Sequence of Testing (C)—The ELC is a recursive battery of subtests in that the protocol presents a progressive sequence of subtests and utilizes information collected early in the subtest battery to determine the starting weight for subsequent subtests in the battery. The ELC provides information about the maximum acceptable weight that the evaluee can lift and lower on "a safe and dependable basis eight to twelve times per day". The ELC uses three vertical ranges (knuckle to shoulder, floor to knuckle, floor to shoulder). Each range is tested separately and in this order so that the biomechanical demand presented by the battery increases gradually and sequentially. It is acceptable to not utilize the complete subtest sequence as long as this order of testing maintained. For example, it would be acceptable to perform only tests #1 and #2 or only tests #2 and #5 as long as this order of testing is maintained. To continue the example, it would not be acceptable to perform test #3 before both test #1 and #2 had been performed or to perform test #4 before test #1 had been performed.

Starting Weight (C)—The ELC utilizes a uniform starting weight of 10 pounds for Test #1 or Test #2. The starting weight for subsequent tests in the battery depends on the evaluee's performance on earlier tests. The starting weight for Test #3 is 70% of the lesser of the maximum achieved in either Test #1 or Test #2. The starting weight for Test #4, Test #5, or Test #6 is 40% of the maximum that was achieved on Test #1, Test #2, or Test #3, respectively. Test #2 is used as a reference for Test #5. Test #3 is used as a reference for Test #6. A lower starting weight may be used at any stage in the process, although the evaluator must realize that, since this violates the assumptions on which the normative data were developed, comparison of the evaluee's performance to the normative database would not be permitted.

Maximum Weight Increment (C)—The weight increment for each additional load for all of the tests in the ELC battery has been standardized at 10 pounds (4.5 kilograms). The same maximum weight increment is utilized for both males and females. In order to maximize the safety of this procedure, the load should not be incremented beyond this weight. However, it may be necessary from time to time to increment the load at a lower level. In such cases, it would not be appropriate to compare this evaluee's performance on this test to the normative database in that the assumption regarding weight load increments was violated.

Frequency Increments (C)—The ELC has been designed to test the evaluee's ability to perform an occasional lift-lower and a frequent lift-lower "eight to twelve times per day on a safe and dependable basis." "Occasional" is defined in the ELC as one lift per cycle, while "Frequent" has been defined in the ELC to be four lifts per cycle. Each cycle is a minimum of 30 seconds. That is, the evaluee may not begin the next lift-lower cycle before 30 seconds has elapsed from the initiation of his or her last lift-lower cycle. Similarly, if the evaluee requires more than a preselected time increment such as 120 seconds after conclusion of the cycle before he or she is able to begin the next lift-lower cycle, the test should be terminated.

Anthrometric Shelf Height Placement (C)—The ELC has been designed to utilize shoulder-height shelves and knuckle-height shelves.

Evaluee's Height (G)—The ELC has been designed to be used by individuals between 58 inches (147 cm) and 77 inches (196 cm) tall.

Evaluee's Weight (G)—The evaluee's absolute weight is not a design criterion of the ELC, although individuals who are significantly obese may not be able to be effectively tested with the use of the High Risk Work Style horizontal displacement factor (see below).

Evaluee's Age (G)—The ELC has been designed to be used with individuals between the ages of 18 years and 60 years, inclusive. At the lower end of the range, heart rate limitations may be insufficient and normative data may not be directly applicable. At the upper end of the range, heart rate limitations may be too restrictive. However, at the evaluator's discretion, the ELC may be used with evaluees above age 60.

Pre-evaluation Screening Limits

In order to minimize the risk involved with the ELC, the evaluator must consider the match between the evaluee and the test battery in terms of the following safety issues:

Medical Stability (C)—The ELC has been designed to be used with individuals whose pathology and impairment is fully understood and has been found to be stable.

Physical impairments (C)—The ELC is designed to be used with healthy individuals and with individuals who have a wide range of physical impairments. However, impairments which result in functional limitations which lead to safety problems e.g., visual impairment, deafness, cardiac impairment, upper extremity impairment, lower extremity impairments, may preclude use of the test.

Appliance Usage (C)—Evaluees who require the use of appliances, orthotic devices, or prosthetic devices should be carefully screened before they are tested on the ELC.

Available Range of Motion (C)—The range of motion that will be involved in any functional test should be assessed so that the evaluator can be certain that sufficient range of motion is available to allow the protocol to be utilized without modification. If the available range of motion is not adequate to use the protocol as presented, the evaluee may be tested on a modified basis. At no time should the evaluator attempt to test the evaluee beyond his/her available range.

Sensibility (G)—If there is an expectation that there will be changes in sensibility, a baseline measure of sensibility should be obtained. Subsequent post-evaluation sensibility testing will reveal whether or not changes have occurred.

Swelling (G)—If the evaluation has a potential to bring about changes in swelling, pre-evaluation and post-evaluation measures should be obtained. Water displacement volumetrics or a similar approach should be utilized.

Evaluee's Understanding of Instructions (C)—If there is any question whether (or not) the evaluee is able to understand instructions, the evaluator should consider not testing. The evaluation should be used only if the evaluee understands the instructions. Instructions should be provided in a language and at a communicative level that is appropriate to the evaluee.

Resting Blood Pressure and Resting Heart Rate (C)—The ELC is not designed to be used by individuals who are hypertensive or who are so physically deconditioned that resting blood pressure exceeds 159/100 and resting heart rate exceeds 90 beats per minute. If the ELC is used with individuals whose blood pressure and heart rate limitations exceed these levels, the ELC should proceed with appropriate monitoring and emergency response capability immediately at hand.

Medication Usage (C)—The ELC should not be performed on people who are taking cardiac rate-limiting medications. Analgesic and anti-inflammatory medications that are used by the evaluee in his/her daily activities should continue to be taken as prescribed but extra care must be given to assist the evaluee to compensate for these effects.

Test Performance Targets and Safety Limits

In order to optimize safety in the ELC, several performance targets and limits have been established. The following limits have been developed to be used to conduct a safe evaluation:

Performance-Limiting Symptoms (C)—Most symptom reports will be non-pathological and will not stop the evaluee from continuing, a least for a brief period of time, should he/she wish to continue. However, if the evaluee experiences new symptoms that indicate a pathological response to the task, the test should be halted and the progression or regression of the symptoms observed. If the symptoms are within the normal range of the evaluee's experience and they subside quickly, the testing may continue. If the symptoms are new to the evaluee and persist, stop the test, the testing should not continue.

Performance Heart Rate Limits (C)—While the ELC is not a test of cardiovascular competence, it may be beyond the evaluee's cardiovascular reserves. For this reason, performance heart rate should be monitored constantly.

Biomechanical Limits (G)—Each of the tests in the ELC battery has a maximum lifting weight based on the evaluee's height (reflecting an ideal body weight) listed as a guideline. If the evaluee achieves this lifting limit without encountering any of the other safety limits in this section, the evaluation may extend beyond this guideline if the performance target for the test has not been achieved.

Lifting Restrictions (C)—Restrictions on lifting which may be imposed on the evaluee by a physician, health care professional, or which the evaluee may have imposed must be respected. The ELC must only be utilized within the context of these restrictions. These restrictions should not be exceeded unless the individual who has provided the restrictions has been consulted. Restrictions that the evaluee has placed on himself or herself may only be exceeded with the expressed permission of the evaluee.

Performance Targets (C)—Each of the six subtests in the ELC battery may have an individual performance target or "target weight" which should not be exceeded without a clear rationale for doing so. If a performance target is not available or is not pertinent, this will not be a limiting factor, and the ELC battery may proceed utilizing only the maximum lifting weight as a lifting limit.

Horizontal Displacement (G)—A high risk work style factor in terms of horizontal displacement is based on the approximate displacement of the center of gravity of the load from the center of the evaluee's spine at the sacrum at the end of each lifting cycle.

Stance (G)—A high risk work style factor in terms of stance has been developed to disallow evaluees to utilize a stance that will lead to imbalance.

Risky Body Mechanics (C)—Body mechanics which indicate that the evaluee has met or exceeded his or her safe maximum are indicators for termination of the test. Examples of these are provided elsewhere herein:

Evaluee's Psychophysical Appraisal (G)—The ELC is designed to be a progressive psychophysical test which assists the evaluee to predict his level of lifting and lowering "on a safe and dependable basis eight to 12 times per day". The evaluator conducts an appraisal at the end of every lift cycle.

Evaluee's Rating of Perceived Load (C)—The evaluee's judgment as to the weight of the load is measured at the end of each lift cycle.

LIFTING CAPACITY TEST

Broadly speaking, the procedures of the methods of the claimed invention can be broken down into three distinct phases. The first phase is a Pre-testing Phase in which specific information relating to the person (the evaluee) is collected and certain personal limiting factors are defined. The second phase is a physical Testing Phase, which is accompanied by monitoring of the evaluee, and the final phase is a Processing and Interpretation Phase in which the data collected during the Testing Phase is analyzed and an interpretation of the evaluee's performance is made. As an optional component to the Testing Phase, the evaluee can complete a Constant Work Test.

The Pre-Testing Phase

During the pre-testing phase, certain evaluee specific information is determined, some of which is used to define limiting factors for the testing conducted in the Testing Phase. This information is entered into a chart similar to the evaluation chart generally indicated as 10 in FIG. 1(a).

Initially, certain demographic information about the evaluee is entered into the top left hand block 12 of the chart 10.

The evaluee's name, age, height, weight, resting blood pressure (RBP) and resting heart rate (RHR) are entered into the respective areas on the first line in block 12. Thereafter, the descriptions of the evaluee's previously incurred injury is entered into the second line of the block 12, along with the date of that injury (DOI). This is followed by entering, onto the third line, any information about the diagnosis of the injury. This information is usually provided by a medical doctor. Finally, any lifting restrictions, once again provided by the doctor, are entered into the appropriate portion (line 4) of the block 12.

A device, more specifically a data recording card, is provided to guide an evaluator in practicing the ELC method. In defining the limiting factors, the age of the evaluee determines the Heart Rate (HR) limits, for any test performed by the evaluee. This is done by using the heart rate selector, wherein the evluator circles the evaluee's age (rounded up to the nearest even number) in the left hand column of insignia displaying the vertical "HR Limits" block 14 on the chart 10. The figures, adjacent the circled age, in the other two columns in the block 14 respectively guide the evaluee to determine the maximum starting heart rate (Start Max) and maximum allowable heart rate (During Max) for the evaluee.

For completeness it is noted that these heart rate limits are independent of the evaluee's gender and are determined by first calculating an absolute maximum heart rate which is defined as 220 minus the age of the evaluee. The maximum starting heart rate for the evaluee is then defined as 70% of the absolute maximum heart rate and the maximum allowable heart rate as 85% of the absolute maximum heart rate.

Furthermore, if the evaluee is below the age of 18, the heart rate limits for age 18 should be used. If the evaluee is over the age of 60, the required heart rate limits must be calculated and the test should only be conducted with special monitoring of cardiac response.

Turning now to the rest of the chart 10, it can be seen that the chart is divided into three vertical subtest sub-divisions 16, 18, and 20. Each of these subdivisions is given a heading representing a range of motion through which an evaluee must lift a test weight. For example, the left most sub-division 16 is headed "Knuckle>Shoulder Target:" which indicates that the evaluee will be required to lift a test weight from knuckle height to shoulder height and back. Next to each subdivision heading, the evaluator enters a target weight, if one exists. This target weight is the actual weight that the evaluee will be required to lift (in the specific lifting range) on a regular basis during a typical work day. This target weight is obtained from a future or past employer, job descriptions, occupational rehabilitation specialists or any other suitable source. In some instances, no target weight will be available, in which case nothing is entered. In such a case, the maximum lifting weight then becomes the sole lifting limit for each test.

Each sub-division, 16, 18, 20 has four columns or recording insignia respectively headed H, S, RPL and HR. As will be explained below in the description of the actual testing procedure, an evaluator enters evaluee data into the blocks in each of these columns. To the right of each of the three sub-divisions, 16, 18, 20, is located lifting limit selectors comprising height/weight tables 22, 24, and 26 respectively, each containing two columns of figures. This height-weight table functions as an indicator for determining the maximum lifting weight for each subtest. Once the evaluee's height (in inches) has been determined and entered in topmost block 12, it is circled in the vertical column headed "Ht" in each of the tables 22, 24 and 26. In order to determine the maximum number of pounds that the evaluee normally is allowed to lift (for that specific range of motion during the testing phase), the evaluator locates this circled height and selects the corresponding weight located in the column of numbers headed "lbs".

It will be noted that the maximum lifting weight guideline shown in two of the tables, 22 and 26, is the same but less than the maximum lifting weight guideline shown in the remaining table 24. It has been knuckle to shoting an object from knuckle to shoulder height is approximately as difficult as lifting the same object from floor to shoulder height, but that it is easier to lift the object from the floor to knuckle height. Accordingly, this chart makes allowance for this by having a greater maximum lifting weight in table 24. The evaluator is guided in properly applying this parameter by the frequency indicia in block 28.

Figure 1D:
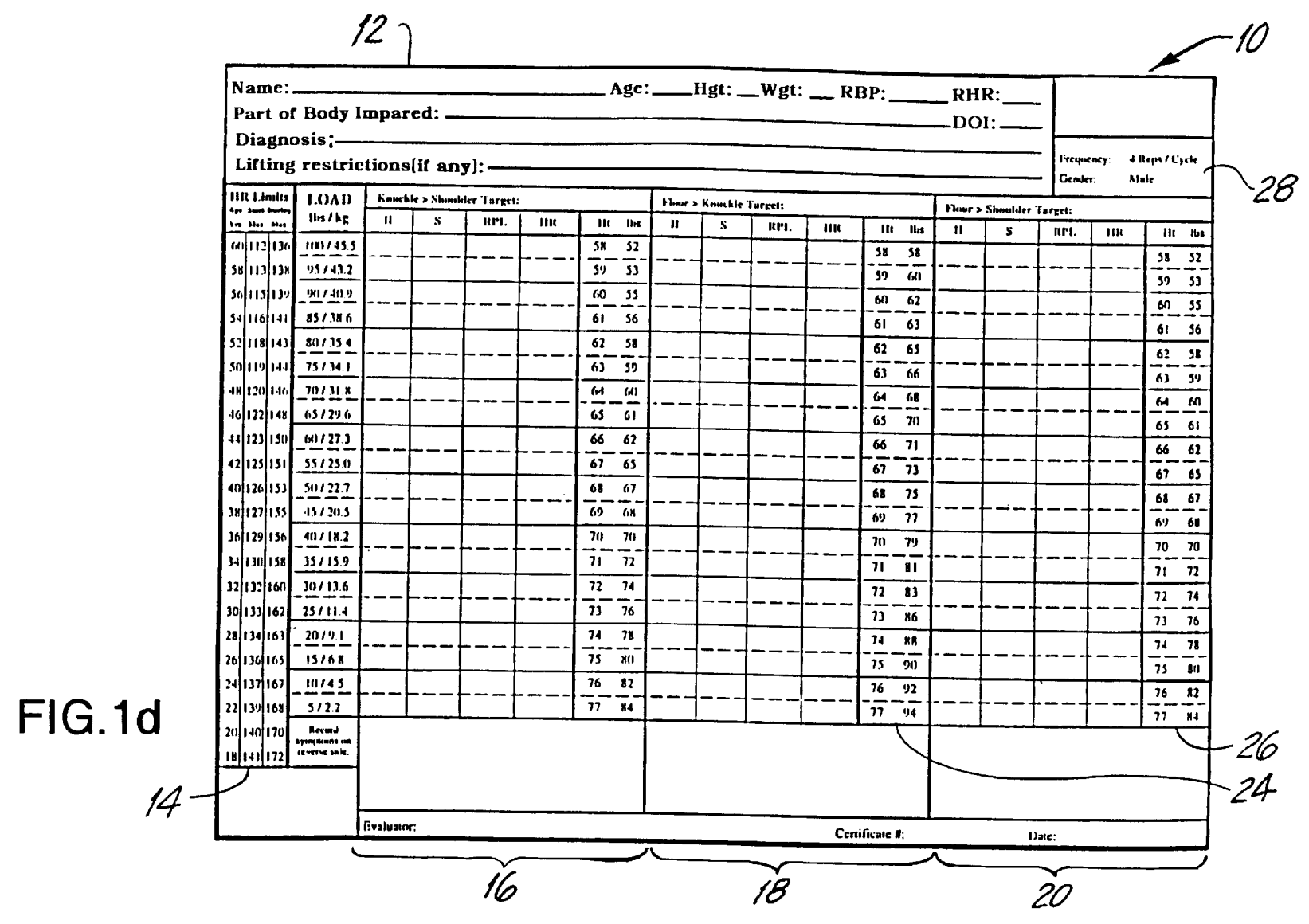
Figure 3:
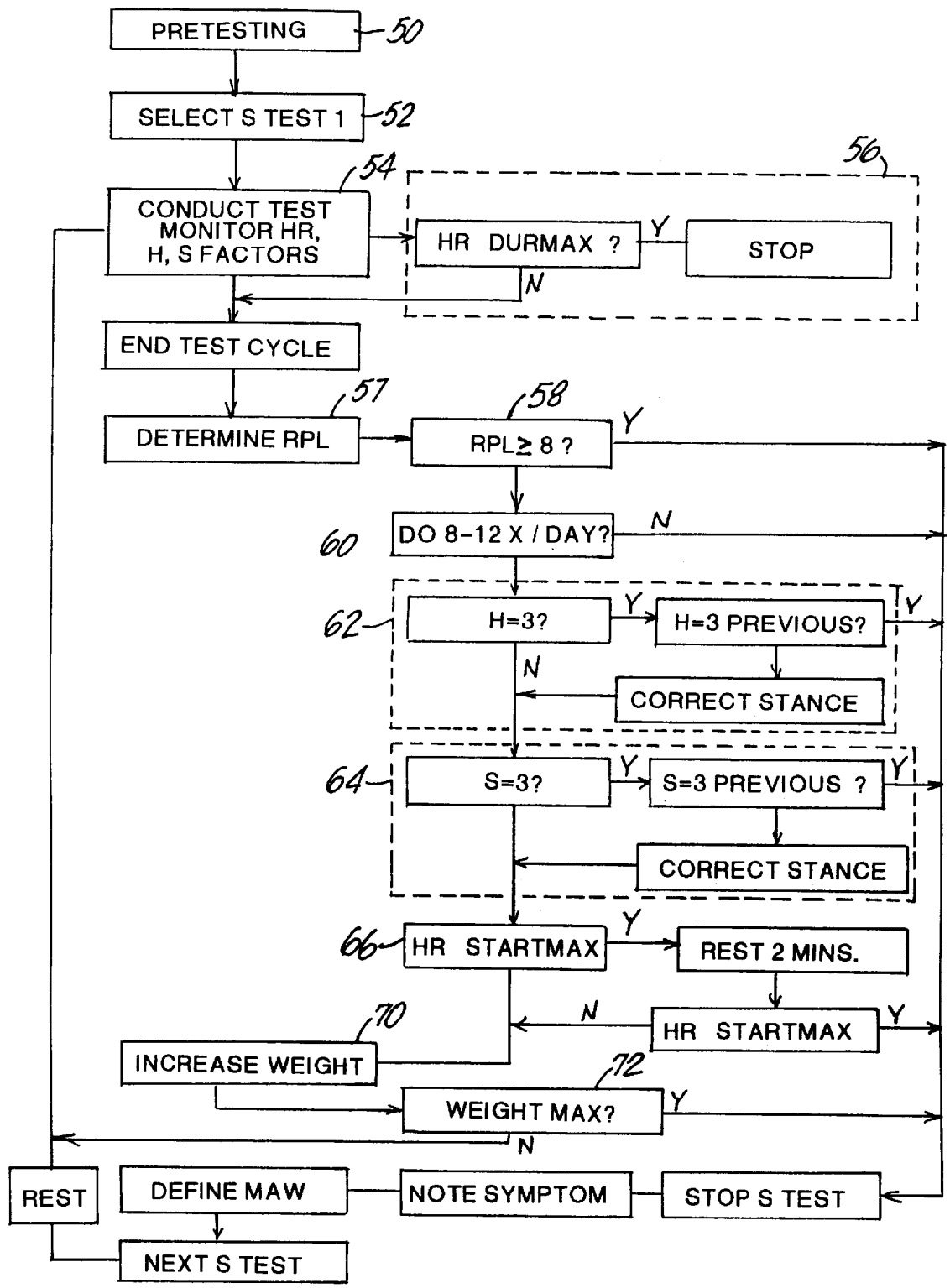
FIG. 3 is a block diagram illustrating the testing phase of the procedure of the invention.

Also, as can be seen from the pre-printed information providing gender insiginia at the top right hand corner block 28, in chart 10, the chart, and in particular the maximum lifting weight, is gender specific. As can also be seen in block 28, a frequency insignia is provided, and is specific to the number of repetitions required in each cycle of a test. Therefore, the chart 10 acts as a device that guides the evaluator in making the proper allowance for both the evaluee's gender and the number of repetitions/cycle, because the gender and frequency indicia determine the correspondingly appropriate lifting limit, i.e., maximum lifting weight varying the lifting weight indicated in the height/weight tables 22, 24 and 26. Each combination of frequency and gender indicia is reflected by a separate chart. The chart 10 illustrated in FIG. 1(a) is for use in recording data for a test having a single repetition/cycle which is conducted on a woman. The charts 10 illustrated in FIGS. 1(b) to 1(d) are respectively used for women in a test with four repetitions/cycle, men in a test with one repetition/cycle and men in a test with four repetitions/cycle. These charts embody each of the ELC method steps, and are designed to control the lifting evaluation at each of the necessary decision nodes. The charts thus embody a very important device that serves both to maximize the safe implementation of the ELC method and the production of valid, reliable data. Although different formats could be used that convey the decisional guidance provided by FIGS. 1(a)–(d), any such embodiment would preferably guide the evaluator through all steps of FIG. 3.

The height/weight tables 22, 24 and 26 have been determined by using standard statistical ideal height-to-weight tables used by the insurance industry (for men and women respectively) and taking defined percentages of these statistical ideal body weights to determine the maximum lifting weights given in these tables. The defined percentages are based on work done by the inventor and by others published in professional literature in which body weight can be related to maximum acceptable weight. This correlation of height/ideal body weight to maximum lifting weight varies across gender, vertical range, and frequency of lift.

Finally, the height range given in these blocks 22, 24 and 26 indicate that the test is designed for testing people who are no shorter than 58 inches (1473 mm) and no taller than 77 inches (1956 mm). If an evaluee's height is outside of this range, the testing procedure could lead to injury or incorrect results. Accordingly, the testing procedure preferably is used for evaluees within this range.

The "target weight" and the "maximum lifting weight" defined by the gender and frequency indicia of height/weight tables 22, 24 and 26 together provide a further limiting factor—the maximum weight or "lifting limit" to be lifted by the evaluee for a specific range of motion. Generally speaking, the evaluee should not lift more weight than the lesser of these two defined weights. If no "target weight" has been determined, the maximum weight defined by the height/weight tables will be the limiting weight. Also, if the "target weight" exceeds the relevant maximum weight defined by the tables, it shows that the target weight may be an unrealistic goal for the evaluee. The evaluee should not be tested above the maximum weight unless the evaluee's response to the test thus far indicates an extraordinary level of lifting work capacity. If the evaluator determines that the evaluee is capable of safely exceeding the lifting limit, then the evaluator may optionally require the evaluee to attempt at least one additional lifting repetition utilizing an increased lifting weight that exceeds the predefined lifting limit.

The resting blood pressure (RBP) and resting heart rate (RHR) are used to pre-screen the person being tested. If either of these two indicators show that the person being tested is at a high risk from a cardiovascular point of view, (i.e., RBP exceeding 159/100 and RHR exceeding 90 beats per minute) testing should not be commenced at all.

As far as the weight of the person tested is concerned, this is used to determine weight related conditions such as excessive obesity and, as a general rule, is not considered a limiting factor in the procedure of this invention. In extreme cases though, excessive obesity may effect the High Risk Work Style Factors (as described below) determined during the test.

Figure 1E:
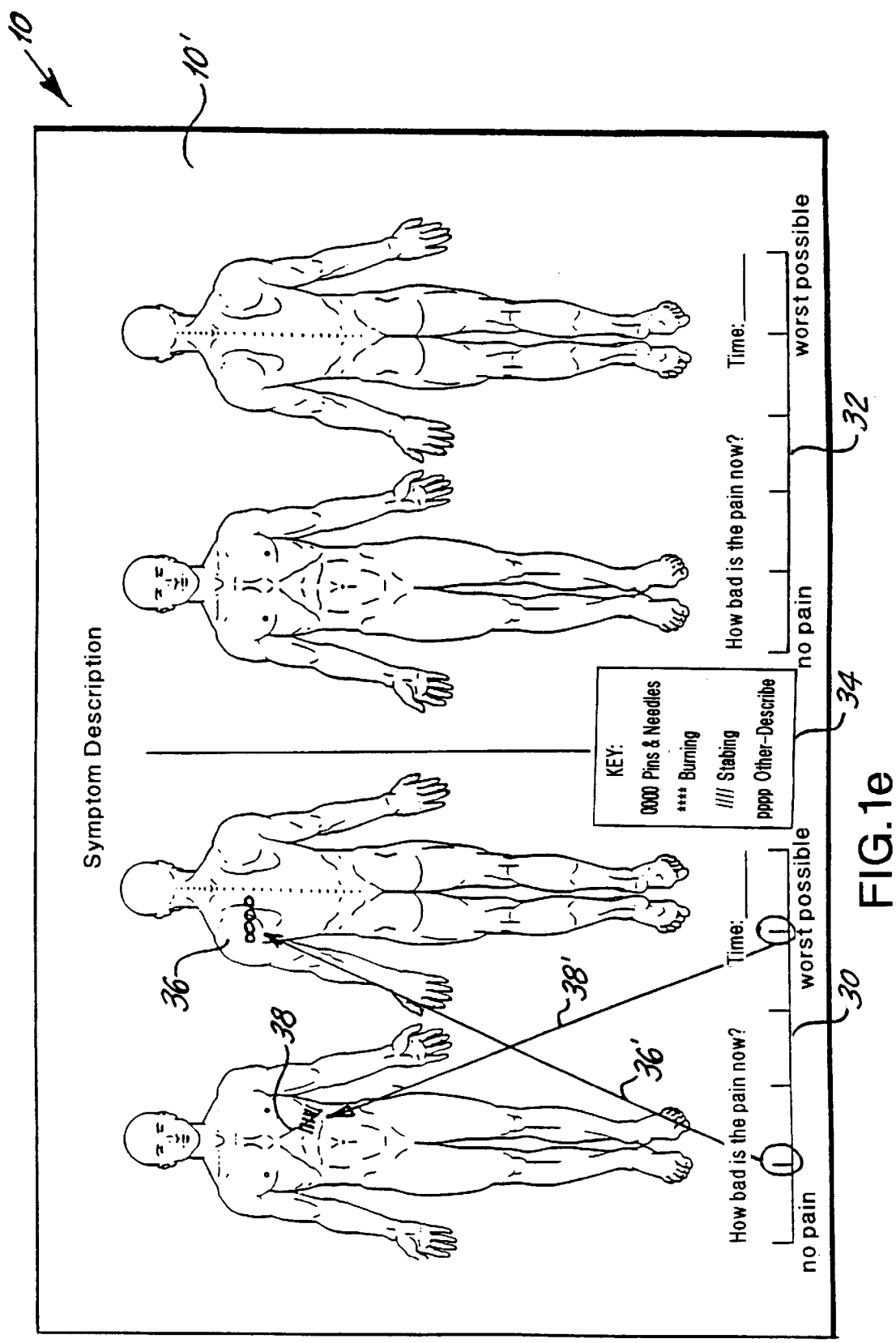
FIG. 1 (e) is a depiction of the backside of any one of the charts illustrated in FIGS. 1(a)–(d)

The back side 10' of the chart 10 is shown, in FIG. 1(e), to be divided into two halves each of which illustrates the front and back of the human body. For each half, a pain indication scale 30, 32 is printed near the bottom of the chart. Before the test commences, the symptomatic conditions of the evaluee are indicated on the illustrations in the left half of the backside 10' of the chart. This is done by choosing appropriate codes, for indicating the pain sensations, felt by the evaluee, from the key 34 located in the center at the bottom of the backside of the chart 10. These pain indicators are then written onto the sketches exactly where they are felt by the evaluee. In this illustrative example, a pins & needles sensation is indicated by '0000' on the left shoulder blade 36 and a stabbing pain by '///////' under the left ribcage 38. The magnitude of the pain for each sensation indicated on the sketches is then circled on the pain indicator scale 30 and a line 36', 38' drawn between the indicator scale 30 and the position 36, 38 of the pain on the body.

The purpose of this recording is to monitor any serious increase in pain that the person being tested may experience so that appropriate recommendations for remedial treatment can be made. Exactly how this is done will become clearer when the Testing Phase is described below.

The evaluation procedure of the invention should be used only with individuals whose pathology and impairment is fully understood and has been found to be stable, i.e., the evaluee must be sufficiently medically stable so that the likelihood of reinjury is minimized. A review of the most recent medical records, contact with the evaluee's physician, or a diagnostic screening assessment (such as the *Cornell Medical Index*) are three different approaches which may be taken to ensure that sufficient medical stability is present so that the evaluee may be tested in the manner (and to the load) that is anticipated. If there are medical contraindications to testing of certain types or if there are physician-imposed restrictions, these must be adhered to and respected.

Although the evaluation procedure of the invention can be used with healthy individuals and with individuals who have a wide range of physical impairments resulting in functional limitations, certain impairments which lead to safety problems may preclude its use. Examples of such impairment and functional limitations include but are not limited to:

a. Visual impairment limiting ability to clearly see appropriate equipment;

b. Deafness leading to auditory limitations that preclude the ability to understand oral instructions;

c. Cardiac impairment that leads to inadequate cardiovascular response to increased activity. This would include individuals who utilize heart rate-limiting medications;

d. Upper extremity impairment leading to functional limitations which preclude adequate grasp of equipment; and e. Lower extremity impairments which result in functional limitations which affect stance, including balance and gait.

When any impairment exists with functional limitations that are not fully understood and/or when impairments exist which may lead to functional limitations that will affect ELC test performance, active screening of the evaluee's musculoskeletal, neurologic, and/or cardiovascular system preferably is undertaken prior to ELC testing.

Once all the above limiting factors have been determined and the other issues addressed, the Testing Phase can commence.

The Testing Phase

The Testing Phase includes six clearly defined progressive and recursive subtests. These subtests are sequentially ordered and are summarized in the following table:

| SUB-TEST | RANGE | FREQUENCY | START WEIGHT |
|---|---|---|---|
| #1 | Knuckle to shoulder | 1x/cycle | 10 lbs. |
| #2 | Floor to knuckle | 1x/cycle | 10 lbs. |
| #3 | Floor to shoulder | 1x/cycle | 70% lesser of #1 or #2 |
| #4 | Knuckle to shoulder | 4x/cycle | 40% of #1 |
| #5 | Floor to knuckle | 4x/cycle | 40% of #2 |
| #6 | Floor to shoulder | 4x/cycle | 40% of #3 |

As is evident from this table, subtests 1 and 4 require the evaluee to lift a selected initial lifting weight from knuckle level (i.e., approximately the level defined by the knuckles when the arm is hanging limp at the side) to shoulder level. Subtests 2 and 5 require lifting between the floor and knuckle levels and subtests 3 and 6 require lifting between the floor and shoulder levels. The first three subtests have only one lift per cycle or "lifting repetition" (i.e., before the weight being lifted is increased) and are recorded on the chart 10 illustrated in either FIGS. 1(a) or 1(c). On the other hand, subtests 4 to 6 have four lifts per cycle or lifting repetition and are recorded on the chart 10 illustrated in either FIGS. 1(b) or 1(d) depending, of course, on the gender of the evaluee.

Although preferable, it is not necessary to sequentially complete each of the 6 subtests. What is important though, is that the subtests must be completed in the order indicated i.e., it is acceptable to move to subtest 3 from subtest 1 but it is not acceptable to move from subtest 4 back to subtest 3.

Also, it should be noted that each lifting repetition in a subtest is a minimum of 30 seconds in duration. That is, the evaluee may not begin the next lift-lower cycle before 30 seconds has elapsed from the initiation of his or her last lift-lower cycle. If, however, the evaluee requires more than 120 seconds after conclusion of the lifting repetition before he or she is able to begin the next lift-lower cycle, the subtest should be terminated.

Figure 15:
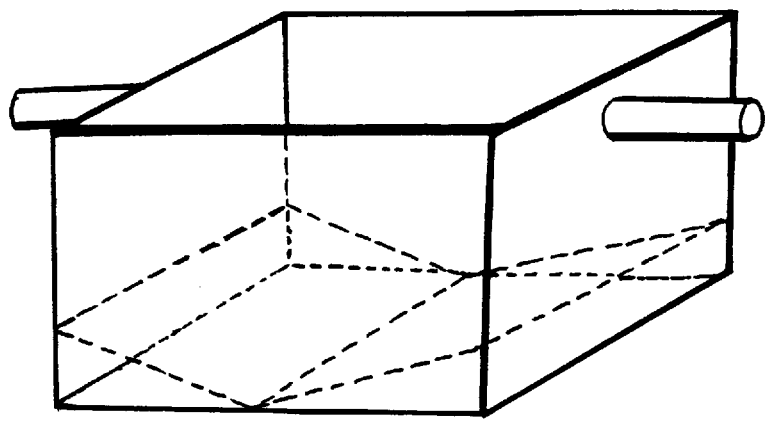
FIG. 15 is a depiction of an evaluative weight container.

The equipment used during the testing phase typically includes five-pound and ten-pound weights and may also include 2½lb. and 15 lb. weights. Each is, preferably a masked weight, approximately 3" in diameter and 11" long. The weights are preferably shaped like canisters, all of indentical size, and are color-coded so that the evalutor, but not the evaluatee, knows the weight to be lifted. During the various subtests these weights are incrementally loaded into an evaluative weight container, preferably a reinforced square crate. The crate is typically 13" by 13", weighs ten pounds and has two handles, one on each of two opposing sides. Preferably, the crate features projecting knurled handles attached to flanges on the crate, so that the wrists of the evaluatee are not unduly strained. An embodiment of this crate is shown in FIG. 15. Preferably, the crate has a base which slopes downwardly from each of the two sides on which the handles are attached so that a central trough is formed near the bottom of the crate. This insures that weights loaded into the crate roll into the trough and are thus prevented from moving around and kept centrally located to minimize weight imbalances on the hands of the evaluee when the crate is lifted.

The equipment also includes a shelving system onto which the evaluee has to lift the crate with weights in it. Preferably, the shelving system has shelves which are at least 36" wide and at least 12" deep. In addition, the shelving system must be such that a first shelf can be located at a level being 27", 30", or 33" above the ground and that a second shelf can be located at a level 48", 54", or 57" above the ground. The shelf heights at 27" and 48" are used to define the knuckle and shoulder heights respectively for evaluees who are no taller than 66"; the shelf heights at 30" and 54" are used to define those levels for evaluees who are from 66" to 72" tall; and shelves located at 33" and 57" to define the levels for people who are over 72" tall.

One of the things that must be monitored during the ELC testing procedure is whether or not the person being tested exhibits high risk work factors. As shown in the table below, these high risk work style factors can be divided into two categories, one relating to the horizontal displacement or distance between the center of gravity of load being lifted and the center of the spine of the evaluee and the other relating to the stance of the evaluee while lifting the load. During each cycle of each subtest, both the H (horizontal displacement) and S (stance) factors are given a rating of 1, 2 or 3 with a rating of 1 indicating that the person being tested is performing appropriately and a rating of 3 indicating that the person being tested is at a significantly increased risk of injury and requires intermediate intervention and correction by the evaluator. How this rating is defined is illustrated in the table below and in FIGS. 2(a) through 2(g).

| | HORIZONAL DISPLACEMENT | STANCE |
|---|---|---|
| | The ability to conserve the horizontal distance between the load and the center of the spine at the sacrum while engaged in work tasks. | The ability to maintain placement of the feet in a broad and stable stance while engaged in work tasks. |
| "1" Decreased probability | Horizontal displacement is within 3 inches of minimum at end of lift. | Feet are shoulder width or greater with forward/rearward |

| | HORIZONAL DISPLACEMENT | STANCE |
|---|---|---|
| of injury. | | placement during lift. |
| "2" Slightly increased probability of injury. | Horizontal displacement is within 6 inches of minimum at end of lift. | Feet are less than shoulder width with forward/rearward placement during lift, or . . . Feet are shoulder width or greater with parallel placement during the lift. |
| | The ability to conserve the horizontal distance between the load and the center of the spine at the sacrum while engaged in work tasks. | The ability to maintain placement of the feet in a broad and stable stance while engaged in work tasks. |
| "1" Decreased probability of injury. | Horizontal displacement is within 3 inches of minimum at end of lift. | Feet are shoulder width or greater with forward/rearward placement during lift. |
| "3" Injury is likely. | Horizontal displacement is beyond 6 inches of minimum at end of lift. | Feet are less than shoulder width with parallel placement during lift. |

Figure 2A:
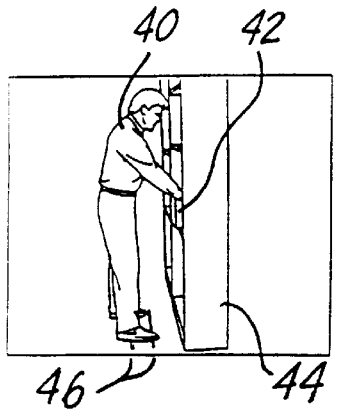
FIGS. 2(a) to (g) are illustrations of various high risk work style factors which can be use in the evaluation method of this invention.
Figure 2B:
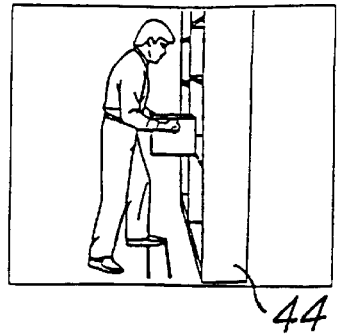
Figure 2C:
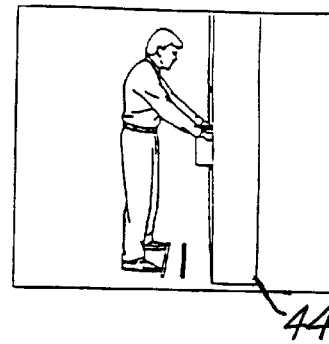
Figure 2D:
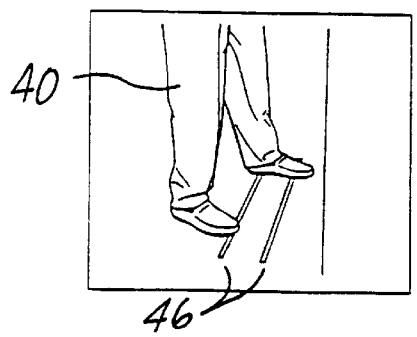
Figure 2E:
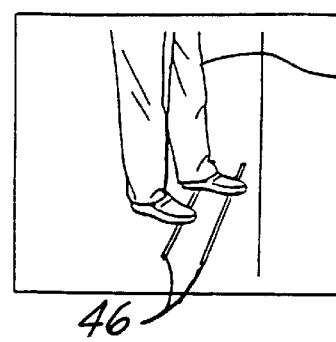
Figure 2F:
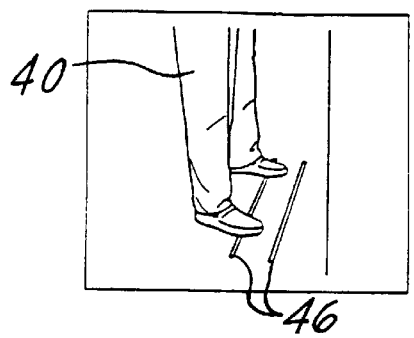
Figure 2G:
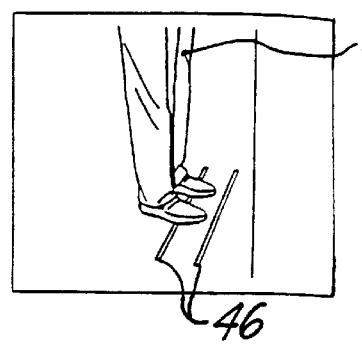

In these figures an evaluee 40 is shown lifting a crate 42 and placing it onto a shelving unit 44. At the feet of the evaluee 40, two parallel lines 46 respectively 3" and 6" from the front of the shelving unit 44, are drawn. As is shown in FIGS. 2(a) to 2(c) these lines are used to define the H factor when the evaluee is lifting the loaded crate 42 onto the shelving unit 44. By referring to the table directly above, it can be seen that, in FIG. 2(a), the H factor for the evaluee 40 is H=1, while the H factor in FIGS. 2(b) and 2(c) is H=2 and H=3 respectively.

The S or stance factors are illustrated in FIGS. 2(d) to 2(g) in which S=1, S=2, S=2, and S=3 respectively. These factors are determined by the positioning of the feet as described in the table. In this stance or foot placement evaluation, the parallel lines 46 assist the evaluator in determining whether or not the feet are side by side or whether they have a forward/rear placement relative to each other, during the lift.

Turning now to the testing procedure itself:

Once the evaluee has had the testing procedure described to him/her, and has completed appropriate warm up and stretch exercises, the evaluee stands in front of the shelving unit and the testing procedure can begin. This procedure is diagrammatically illustrated in the block diagram in FIG. 3. This figure which the top most block 50 labelled "Pretesting" refers to the pre-test phase described above. The Testing Phase itself is commenced, as indicated by block 52, by selecting the appropriate subtest.

Typically, subtest 1 is selected first followed by the remaining subtests in numerical order. Subtest 1 (as previously described) has one lift per lifting repetition and begins with an empty crate, i.e., a lift weight of 10 pounds. In this subtest, the evaluee is required to lift the crate from a first shelf at approximately knuckle height to a second shelf at approximately shoulder height and, thereafter, return the crate back to the first shelf.

During this subtest, as indicated by block 54, the heart rate of the evaluee as well as the evaluee's H and S factors are monitored and noted to ensure that the evaluee is not injured. As indicated by the steps included in the first heart rate decision block 56, if the evaluee's heart rate exceeds the maximum testing heart rate (DurMax) at any time during the subtest cycle, the entire test procedure must be stopped immediately.

Directly after the first cycle of the subtest, and as represented by block 57, the evaluee is asked to rate the perceived load by answering the question "How much does this weigh?" according to the following scale:

1—Like nothing at all.
2—Very light.
3—Light.
4—Light to medium.
5—Medium.
6—Medium to heavy.
7—Heavy.
8—Very heavy.
9—Extremely heavy.
10—Too heavy.

The evaluee's response to this question yields an RPL factor. The H, S, RPL and heart rate (HR) factors/readings are then entered into the corresponding recording insignia in the subdivision 16 of the form 10 (illustrated in FIG. 1) corresponding to a lifted load of 10 lbs. (4.5 kg.)

The chart 10 provides systematic guidance in assisting the evaluator in properly applying the ELC method. As shown by decision block 58, the test must be stopped if the RPL factor is greater than or equal to 8. If the RPL factor is equal to 8 and the evaluee believes the weight can be lifted eight to twelve times per day, the maximum acceptable weight is the weight lifted in the cycle in question. However, when the subtest is stopped because the RPL factor is greater than 8, or if the evaluee believes that the weight cannot be lifted eight to twelve times per day (and RPL=8) the maximum acceptable load will be defined as the load lifted in the previous cycle of the same subtest. In this case, as it is the first cycle of the subtest, this will define a maximum acceptable load of zero pounds. In any event, irrespective of the RPL factor, and as represented by block 60, if the evaluee answers in the negative to the question of whether he/she can perform the just completed lift cycle between 8 to 12 times per day, the subtest must be terminated. Here, as with an RPL factor of 8, the maximum acceptable weight will be the weight lifted in the cycle in question.

If the evaluee answers in the affirmative, as indicated by the steps shown in decision blocks 62 and 64, a check must be made to see whether either of the H or S factors provided by the high risk work style recording insignia is equal to 3. If either of these factors is equal to 3 and the same factor was equal to 3 in a previous lift cycle of the same subtest, then the test must be stopped. In this case, the maximum acceptable weight will be the weight lifted in that cycle. If, however, the H or S factors are equal to 3 (and sometimes when they are equal to 2) for the first time in the subtest, then the evaluee must be shown how to correct his/her stance and/or body mechanics.

Once that is done, the measured heart rate (HR) must be compared to the maximum starting heart rate (Start Max). The evaluator is guided in this analysis by the second heart rate decision block 66 of the chart 10. If the evaluee's heart rate exceeds the starting maximum heart rate at the end of one lift cycle, the evaluee must be allowed to rest for a maximum period of two minutes before the next lift cycle of the selected subtest can be commenced. If the heart rate continues to exceed the maximum starting heart rate after a two minute standing rest then the subtest must be terminated and preparations made for the next selected sequential subtest. In this case, the maximum acceptable weight (MAW) for the first subtest must be defined as the load in the previous successfully completed lifting repetition. However, the next test should not be commenced with a heart rate greater than the maximum starting heart rate (Start Max) so the evaluee must be allowed to rest until this happens.

If, after the two minute rest the evaluee's heart rate has subsided to below the maximum starting heart rate, the evaluator may require the evaluatee to perform another lifting repetition within the selected subtest. This is done by increasing the lifting weight in the crate by a further 10 lbs and checking to see whether this new lifting weight is greater than the lifting limit. First, the evaluator determines whether the maximum lifting weight has been exceeded. The evaluator makes this determination with the guidance of decision blocks 70 and 72. If the maximum weight is exceeded, the subtest must be terminated unless the target weight is greater than the maximum lifting weight and the evaluee's response to the test indicates an extraordinary level of lifting work capacity. If, however, these weight limitations are not exceeded, and the evaluee believes he/she can safely lift the increased weight, the next lifting repetition of same subtest can be recommenced at block 54.

As is evident from the figure and the above description, the subtest is continued until one of the described limiting factors is generated. At that time, the evaluator is guided by chart 10 in defining the maximum acceptable weight for the subtest, and notes any symptomatic conditions reported by the evaluee in the open block of portion 16 on the form 10.

Once the evaluee has been allowed to rest, typically for two minutes, the crate is unloaded and progressive subtest 2 (i.e. lifting the crate from the floor to knuckle level) is commenced. This subtest follows exactly the same procedure as subtest 1 and is recorded in the second sub-division 18 of the chart 10. Similarly, for sequential subtest 3, the evaluee follows the same procedure as previously described and the results are recorded in the third subdivision 20 of the chart. The only difference is that, in subtest 3, the evaluee has a initial lift weight of 70% (rounded to the nearest five pounds) of the lesser of the maximum acceptable weights generated by either subtest 1 or 2.

Thereafter, subtests 4, 5 and 6 are sequentially conducted. These tests have the same ranges of motion as subtests 1, 2 and 3 respectively. However, in these subtests the evaluee is required to complete four lift and lower movements per cycle of each subtest and the evaluator uses a slightly different chart (either FIGS. 1(*b*) or 1(*d*)), reflecting the proper frequency and gender indicia, to record the results. Another difference is that each subtest 4, 5, and 6 is started with a weight of no more than 40% (rounded to the nearest five pounds) of the maximum acceptable weight defined in its corresponding subtest 1, 2 or 3.

In addition, to the above numerically defined factors, an evaluator preferably observes the evaluee's body mechanics during the test to determine if the load has exceeded the safety limit. Body Mechanics which indicate that the evaluee has met or exceeded a safe maximum load are indicators that a subtest should be terminated. Examples of these are:

a. Twisting the spine to move the load from one shelf to another or from the floor to the shelf;
b. Throwing the load up from one shelf to the next or from the floor to a shelf;
c. Dropping the load from one shelf to the next or from a shelf to the floor;
d. Sliding the load over the front edge of the shelf;
e. Flexing or extending the spine in an active whiplash-type motion while lifting or lowering the load; and
f. Using either lower extremity to "nudge" the load from floor level to either shelf. Using the pelvis to push the load onto the lower shelf is acceptable however.

Once the selected progressive subtests have been completed (or when an evaluee is unable to continue any form of testing), the evaluator records the symptomatic conditions of the evaluee on the figures on the right half of the back 10' of the chart 10 shown in FIG. 1(e). This recording is done using the same pain-type key 34 and scale 32 as used to record on the figures on the left half of the chart.

The Processing and Interpretation Phase

The next phase of the evaluation procedure is the processing and interpretation phase.

Normative Percentile Rankings

Research has been conducted with the ELC on normal healthy males and females, disabled males and females, and on experimental subjects who have been specially screened for health and fitness. The normative data for the healthy and experimental subjects are presented in FIGS. 4–6. The evaluator will find that FIGS. 4 and 5 will be important references in determining the evaluee's performance ranking. FIG. 4 is based on 64 healthy females 18 to 44 years old with a mean age of 28.7 years. These women averaged 64.8 inches in height and weighed an average of 133.2 pounds. FIG. 5 is based on 96 healthy males 18 to 51 years old with a mean age of 30.3 years. These men averaged 69.9 inches in height and weighed an average of 175.8 pounds. Subjects in these two reference groups were selected from the normal population, screened with the standard criteria presented in this description, and tested on the ELC in the standard manner. Subjects in the experimental groups were more rigorously screened and tested without heart rate or RPL performance limits. These data are provided for reference only.

Maximum Acceptable Weight (MAW)

If the evaluee is to be compared with other individuals or groups of individuals generally, then the maximum acceptable weight is used to directly rank the performance of that evaluee for each subtest. This is done by taking the maximum acceptable weight for each subtest and reading off a corresponding percentile value for that test from the appropriate normative table shown in either FIG. 4(a) or FIG. 5(a). The table in FIG. 4(a) is used for female evaluees and the table in FIG. 5(a) for male evaluees.

The maximum acceptable weight on a sub-test by sub-test basis will also be useful in those cases in which the ELC is used as part of a job-specific work tolerance screening or functional capacity evaluation comparing the evaluee's performance to the demands of a particular job or occupation. Rather than report a percentile ranking which would compare the evaluee to the performance of other same-gender workers, the MAW is simply compared to the job's demands over each of the vertical ranges and frequencies of the ELC. If the exact vertical range and frequency was not tested, an approximation can be attempted. If the discrepancy between the job task's vertical range and/or frequency is too great, a subsequent work simulation test using the ELC as a pre-screening test may be appropriate.

Relative Acceptable Weight (RAW)

If it is necessary to describe the performance ranking of the evaluee in a relative way based on the evaluee's body mass, then a relative acceptable weight calculation must be done for each subtest. This is done by dividing the maximum acceptable weight for a subtest by the body weight of the evaluee. This number is then compared to either of the normative tables in FIGS. 4(b) or 5(b) (depending on the evaluee's gender) to read off a relative acceptable weight percentile. This provides a measure of lift capacity that is normalized by body size. It allows comparison among people of various sizes and tends to minimize (but not completely do away with) gender differences in lift performance. If it is necessary to describe performance based on the evaluee's body mass, the relative acceptable weight on a sub-test by sub-test basis is the proper comparison. This is most useful when changes in the evaluee's performance are going to be compared over time as in a rehabilitation program. A baseline measure of performance is collected at the start of the program. Periodically, the evaluee is retested and improvement is recorded.

Either or both of these percentile readings can be used to determine whether or not the evaluee can benefit from a rehabilitation program. For example, if the evaluee is in the 25th percentile on both tables, rehabilitation programs such as a work conditioning program would in all likelihood improve the evaluee's ability to do the required work. If, on the other hand, the evaluee ranks in the upper percentiles, above 75th or 80th percentile, then it is unlikely that this evaluee would be able to further improve.

Physical Demand Characteristics Chart Interpretation

In this approach to interpretation of test results, the evaluee's performance on Test #3 is of primary importance. The maximum acceptable weight for the evaluee on Test #3 is interpreted in terms of the rating in the "occasional" column on the Physical Demand Characteristics (PDC) chart which appears below. Test #1 through Test #3 in the ELC have been designed to provide fair and accurate estimates of the evaluee's performance in occasional lifting as defined in the PDC chart. Test #3 is selected as the key to the interpretation because it is a test over the full vertical range. In addition, the evaluee's performance on Test #6 must correspond to the requirement under the "frequent" column on the PDC chart. If the evaluee's performance is substantially below that level on Test #6, the next lighter PDC level is selected.

If the evaluee's heart rate has been adequate during testing and the evaluee does not have any cardiovascular or metabolic limitations, the results of the above subtests are such that the evaluee's ability to perform work at a constant demand level can often be assumed. In some instances, however, it may be important for the evaluee to be subjected to a constant work test.

| PHYSICAL DEMAND CHARACTERISTICS (PDC) CHART | | | | |
|---|---|---|---|---|
| PHYSICAL DEMAND LEVEL | OCCASIONAL 0–33% of the workday | FREQUENT 34–66% of the workday | CONSTANT 67–100% of the workday | TYPICAL ENERGY REQUIRED |
| SEDENTARY | 10 lbs | Negligible | Negligible | 1.5–2.1 METS |
| LIGHT | 20 lbs | 10 lbs and/or | Negligible and/or | 2.2–3.5 METS |

PHYSICAL DEMAND CHARACTERISTICS (PDC) CHART

| PHYSICAL DEMAND LEVEL | OCCASIONAL 0–33% of the workday | FREQUENT 34–66% of the workday | CONSTANT 67–100% of the workday | TYPICAL ENERGY REQUIRED |
|---|---|---|---|---|
| | | Walk/Stand/ Push/Pull of Arm/Leg controls | Push/Pull of Arm/Leg controls while seated | |
| MEDIUM | 20 to 50 lbs | 10 to 25 lbs | 10 lbs | 3.6–3.3 METS |
| HEAVY | 50 to 100 lbs | 25 to 50 lbs | 10 to 20 lbs | 6.4–7.5 METS |
| VERY HEAVY | Over 100 lbs | Over 50 lbs | Over 20 lbs | Over 7.5 METS |

The Constant Work Test

As an introduction to the constant work test, it is noted that the United States Department of Labor has defined five categories of work with different amounts of weights that need to be moved on occasional, frequent and constant bases. These definitions are summarized in above PDC Chart.

The Constant Work Test is completed after the Lifting Capacity Test described above. As a first step, the category of constant work must be defined from the above PDC Chart. If an evaluee is required to do only sedentary or light work then it is unnecessary to complete constant work test. If, however, the evaluee is going to be required to do medium, heavy or very heavy work a test load must be selected. For medium work the test load is ten pounds and for heavy work the test load is 20 pounds. For very heavy work, a test load equal to 30% of the maximum "occasional load" in terms of the above table must be calculated.

Thereafter, a shoulder height shelf must be chosen according to the evaluee' height in the same manner as in the test phase described above. Heart rate monitoring equipment is then attached to the evaluee who is thereafter required to lift the test weight from floor level to shoulder level and return it to the floor level at a rate of about three lifts per minute.

During the initial monitoring phase, the lifting exercise is done for about five minutes. The heart rate of the evaluee is very carefully monitored to ensure that it does not exceed the Start Max limit. If the Start Max limit is exceeded at three lifts per minute, the constant work test should be terminated and a conclusion can be drawn that the evaluee is not sufficiently fit to perform constant work with the test load. If, on the other hand, the evaluee' heart rate response remains below the Start Max rate during the initial monitoring phase, the evaluee enters the testing phase. The evaluee is required to continue the exercise for a period of 2 hours of continuous work. During this test, the evaluee should increase the rate of work to a maximal frequency at which he/she can maintain his/her rate of work at an even and comfortable pace for up to two hours.

In this test the number of lift and lower cycles that the evaluee completes must be monitored. This number is then compared to one of the two normative tables shown in either 13(a) or 13(b). FIG. 13(a) is to be used for a test relating to a medium physical demand level test while FIG. 13(b) is to be used for a heavy or very heavy physical demand test. These tables can be used to indicate what the M.T.M. (Method Time Measurement) percentage the evaluee falls in. If the evaluee has completed two hours of work the number of repetitions is looked up in the appropriate column of the appropriate table and the M.T.M. percentage can be read off. This percentage then acts as a reliable measure of suitability of the evaluee for doing the measured type of constant work.

As can be seen from the tables in FIG. 6(a) and 6(b), it is not necessary to do the test for a full two hours. It is, however, preferable to do so as the full two hour test leads to more accurate results than a test of, say, fifteen minutes.

CASE EXAMPLES

The first two examples presented below are presented in terms of sets of information. The first set of information involves qualifying statements that address high risk work style factors, attitude factors, degree to which evaluee put forth full effort, and other aspects of the test performance that are based on the evaluator's behavioral observations. The second set of information is the actual test results presented in terms of percentile rankings compared with appropriate normative groups as well as the comparison to the physical demand characteristics chart and any job target information that is available. Examples 3 and 4 reflect the results of studies evaluating the safety and reliability of the ELC protocol.

Example 1

Figure 7:
FIGS. 7 to 9 illustrate the invention by means of a worked example using the charts of FIGS. 1(a) and 1(c) for a woman.

Mary Smith is a 46-year-old 120-pound female who has been off of work from her job as a Parts Handler at ABC Manufacturing for six months. She has been diagnosed as suffering a back strain with mild degenerative disc disease. She has pain with activity but is medically stable. She enters the rehabilitation program and undergoes baseline testing. The ELC Infrequent Evaluation Record is replicated in FIG. 7 of the attached drawings.

Smith Report #1 Excerpt

In order to evaluate Ms. Smith's lift capacity in a manner that would be safe, reliable and valid, the EPIC Lift Capacity test was utilized. Pertinent results are presented in the table below:

| Test | Range | Frequency | MAW | % tile | RAW | % tile |
|---|---|---|---|---|---|---|
| 1 | Knuckle to Shoulder | 1/cycle | 30 lbs | 25th | .25 | 40th |
| 2 | Floor to Knuckle | 1/cycle | 20 lbs | <10th | .17 | <10th |
| 3 | Floor to Shoulder | 1/cycle | 30 lbs | 25th | .25 | 30th |
| 4 | Knuckle to Shoulder | 4/cycle | 20 lbs | 10th | .17 | 10th |
| 5 | Floor to Knuckle | 4/cycle | 10 lbs | <10th | .08 | <10th |
| 6 | Floor to Shoulder | 4/cycle | unable | — | — | — |

Smith's body mechanics were unacceptable and required correction during Test #1. She responded to the correction and was allowed to continue. Her heart rate response to the tasks indicates that she put forth full effort.

Ms. Smith's symptom responses to the tasks consisted of "achey" pain in the lumbar area without radiation. These occurred dependably during the tests that involved spinal flexion and extension from a flexed posture and were tolerable to her. She fatigued considerably over the course of the test battery and was unable to safely complete all four repetitions of Test #6 at the beginning weight of 10 pounds.

Ms. Smith's maximum acceptable weight is 30 pounds on an occasional basis over a full range of motion. She is too de-conditioned to safely and dependably lift-lower frequently at any load over her full range.

Ms. Smith appears to be able to benefit from a rehabilitation program. We recommend a four-week work conditioning program to improve lift capacity with a retest at two weeks to confirm progress. If she is making significant progress, consideration should be given to attempting a return to work at ABC Manufacturing. A job analysis of the Parts Handler job at ABC will be necessary at that time.

Figure 8:

After two weeks in the rehabilitation program, Ms. Smith was retested. The ELC Frequent Evaluation Record is replicated in FIG. 8 of the attached drawings.

Smith Report #2 Excerpt

In order to evaluate Ms. Smith's lift capacity in a manner that would be safe, reliable and valid, the EPIC Lift Capacity test was utilized. Pertinent results are presented in the table below:

| Test | Range | Frequency | MAW | % tile | RAW | % tile |
|---|---|---|---|---|---|---|
| 1 | Knuckle to Shoulder | 1/cycle | 30 lbs | 25th | .25 | 40th |
| 2 | Floor to Knuckle | 1/cycle | 40 lbs | 25th | .33 | 40th |
| 3 | Floor to Shoulder | 1/cycle | 30 lbs | 25th | .25 | 30th |
| 4 | Knuckle to Shoulder | 4/cycle | 20 lbs | 10th | .17 | 10th |
| 5 | Floor to Knuckle | 4/cycle | 25 lbs | 10th | .21 | 10th |
| 6 | Floor to Shoulder | 4/cycle | 20 lbs | 25th | .17 | 10th |

Ms. Smith's high risk work style was acceptable throughout. She consistently demonstrated good body mechanics. Her heart rate response to the tasks indicates that she put forth full effort.

As in the initial lifting test two weeks previously, her symptom responses to the tasks consisted of "achey" pain in the lumbar area without radiation. These occurred dependably during the tests that involved spinal flexion and extension from a flexed posture during the frequent tests only. These symptoms were tolerable to her.

Ms. Smith's maximum acceptable weight is 30 pounds on an occasional basis over a full range of motion. Her maximum acceptable weight is 20 pounds on a frequent basis over a full range of motion, representing significant improvement in fatigue tolerance.

Ms. Smith has improved substantially over the first two weeks in work conditioning. We recommend continued participation to the conclusion of the program after an additional two weeks. A job analysis will be necessary to determine whether it is appropriate to consider a return to work as a Parts Handler at ABC Manufacturing.

Figure 9:

Based on this report, a job analysis was performed. It reveals that Ms. Smith's job requires occasional lifting of up to 50 pounds from floor to shoulder level and frequent lifting of 10 to 20 pounds from floor to knuckle level. After an additional two weeks in the rehabilitation program, Ms. Smith was retested. The ELC Frequent Evaluation Record is replicated in FIG. 9 of the attached drawings.

Smith Report #3 Excerpt

In order to evaluate Ms. Smith's lift capacity in a manner that would be safe, reliable and valid, the EPIC Lift Capacity test was utilized. Pertinent results are presented in the table below:

| Test | Range | Frequency | MAW | % tile | RAW | % tile |
|---|---|---|---|---|---|---|
| 1 | Knuckle to Shoulder | 1/cycle | 50 lbs | 75th | .42 | 90th |
| 2 | Floor to Knuckle | 1/cycle | 60 lbs | 75th | .50 | 75th |
| 3 | Floor to Shoulder | 1/cycle | 50 lbs | 80th | .42 | 70th |
| 4 | Knuckle to Shoulder | 4/cycle | 30 lbs | 40th | .25 | 50th |
| 5 | Floor to Knuckle | 4/cycle | 35 lbs | 40th | .29 | 40th |
| 6 | Floor to Shoulder | 4/cycle | 30 lbs | 50th | .25 | 45th |

Ms. Smith's high risk work style was acceptable throughout. She demonstrated excellent body mechanics. Her heart rate response to the tasks indicates that she put forth full effort.

As in previous lifting tests, her symptom responses to the tasks consisted of "achey" pain in the lumbar area without radiation. However, these were much less pronounced than during the last test and were well controlled with simple stretching while standing between the test trials.

Ms. Smith's maximum acceptable weight is 50 pounds on an occasional basis over a full range of motion. Her maximum acceptable weight is 30 pounds on a frequent basis over a full range of motion. This corresponds to work at the "Medium" physical demand characteristics level as defined by the United States Department of Labor and depicted in the chart that is enclosed with this report.

Ms. Smith has improved substantially over the course of the work conditioning program. We recommend a one-week full-day work simulation of the Parts Handler job at ABC Manufacturing. Based on her performance, it appears likely that she will be able to return to her usual and customary employment.

A conference is held with Ms. Smith's worker's compensation insurance claimsperson, therapist. employer, and rehabilitation counselor. Ms. Smith's employer is concerned that she may not actually be able to handle the demands of the job on an all-day basis. In response to this concern, and based on the recommendation from the therapist, a one-week full-time work simulation is authorized by the insurance claimsperson.

The therapist and employer representative coordinate on how best to prepare the work simulation. The employer lends selected work tools and surplus parts to the therapist to improve the validity of the work simulation.

Ms. Smith participates in the work simulation on a full-time basis, simulating the daily schedule, lift/carry/stand/walk, and energy demands of her job at the rehabilitation center.

After one week of work simulation, Ms. Smith is tired but has demonstrated that she can handle the job without undue fatigue that would place her at increased risk of re-injury.

Based on Ms. Smith's performance, the therapist recommends to the physician that Ms. Smith be cleared to return to work. The physician concurs. Ms. Smith successfully returns to work.

Example 2

Thomas Jones is a 46-year-old 180-pound male who has been diagnosed as suffering from a head injury and soft-tissue injury to the cervical spine. Prior to the injury, he was a warehouseman for XYZ Shipping. However, he has been off of work for 18 months and this job may no longer be available.

Mr. Jones is medically stable. The head injury has produced minor cognitive limitations but has brought about significant difficulties with judgment specifically involving self-protective behavior. The injury to the cervical spine has brought about slight loss of strength in the right dominant upper extremity and complaints of pain in the cervical spine followed by severe headaches.

Figure 10:
FIGS. 10 to 12 illustrate the invention by means of a worked example using the charts of FIGS. 1(b) and 1(d) for a man.

Mr. Jones would like to return to his previous job but does not think he will be able to do so. He is discouraged and morose. He enters the rehabilitation program and undergoes baseline testing. His Infrequent Evaluation Record is presented in FIG. 10 of the attached drawings.

Jones Report #1 Excerpt

In order to evaluate Mr. Jones's lift capacity in a manner that would be safe, reliable and valid, the EPIC Lift Capacity test was utilized. Pertinent results are presented in the table below.

| Test | Range | Frequency | MAW | % tile | RAW | % tile |
|---|---|---|---|---|---|---|
| 1 | Knuckle to Shoulder | 1/cycle | 30 lbs | 10th | .17 | <10th |
| 2 | Floor to Knuckle | 1/cycle | 40 lbs | 10th | .22 | <10th |
| 3 | Floor to Shoulder | 1/cycle | 30 lbs | <10th | .17 | <10th |
| 4 | Knuckle to Shoulder | 4/cycle | — | | — | |
| 5 | Floor to Knuckle | 4/cycle | — | | — | |
| 6 | Floor to Shoutder | 4/cycle | — | | — | |

Mr. Jones's primary limitation in lifting is his safety judgment. He demonstrated high risk work style behaviors which required correction by the evaluator. Even with this correction, he continued to demonstrate these behaviors. He was judged sufficiently unsafe that the evaluation was concluded after three of the six planned tests.

Mr. Jones's symptom responses to the test consisted of tightness and aching in the right cervical spine extending into the occiput. He was encouraged to gently stretch this area. Over a thirty-minute period during which he was monitored, these symptoms stabilized and receded.

Mr. Jones's heart rate response indicates that he put forth full effort on those tests that he was able to complete. There was no indication that the weakness in the right upper extremity limited him or produced problems independent of the high risk work style factors.

Mr. Jones appears to be able to benefit from a rehabilitation program. We recommend a one-week work hardening trial to improve safety with a retest to confirm progress. If he is making significant progress, consideration should be given to attempting a return to work at XYZ Shipping.

Figure 11:

Mr. Jones entered a work hardening program which focused on developing his physical capacity on a safe and dependable basis. Although he had some difficulty, he responded well and, after one week, was retested. An ELC Frequent Evaluation Record is replicated in FIG. 11 of the attached drawings.

Jones Report #2 Excerpt

In order to evaluate Mr. Jones's lift capacity in a manner that would be safe, reliable and valid, the EPIC Lift Capacity test was utilized. Pertinent results are presented in the table below:

| Test | Range | Frequency | MAW | % tile | RAW | % tile |
|---|---|---|---|---|---|---|
| 1 | Knuckle to Shoulder | 1/cycle | 60 lbs | 40th | .33 | 25th |
| 2 | Floor to Knuckle | 1/cycle | 70 lbs | 50th | .39 | 30th |
| 3 | Floor to Shoulder | 1/cycle | 50 lbs | 20th | .28 | 20th |
| 4 | Knuckle to Shoulder | 4/cycle | 45 lbs | 20th | .25 | 20th |
| 5 | Floor to Knuckle | 4/cycle | 50 lbs | 25th | .28 | 25th |
| 6 | Floor to Shoulder | 4/cycle | 40 lbs | 15th | .22 | 20th |

Test results indicate that Mr. Jones is a much safer and more dependable worker. He demonstrated no high risk workstyle problems. His symptom responses to the test activities were similar to those of his first test trial. He utilized the cervical stretch procedure spontaneously, with good effect in terms of symptom control.

Mr. Jones's maximum acceptable weight is 50 pounds on an occasional basis over a full range of motion. His maximum acceptable weight is 40 pounds on a frequent basis over a full range of motion.

Mr. Jones has improved substantially over the first week in work hardening. We recommend continued participation in the program. A job analysis is necessary to determine whether it is appropriate to consider a return to his original job as a warehouseman at XYZ Shipping. The work hardening program will be customized to simulate these work demands.

In collaboration with Mr. Jones's rehabilitation counselor, a job analysis is conducted. This reveals that this job requires lifting 80 pounds from floor to shoulder occasionally, 50 pounds from floor to shoulder frequently, and 20 pounds from floor to waist constantly.

A work simulation is set up within the parameters developed by his performance in the ELC test. The work simulation requires that Mr. Jones lift 60 pounds from floor to shoulder occasionally, 35 pounds from floor to shoulder frequently, and 15 pounds from floor to waist constantly.

Mr. Jones performs his work simulation once each day for two hours as part of his work hardening program. His heart rate responses are adequate. After one week, the constant load is increased to 20 pounds, which he tolerates well.

Figure 12:

After an additional two weeks in the rehabilitation program, Mr. Jones was retested. An ELC Frequent Evaluation Record is replicated in FIG. 12 of the attached drawings.

Jones Report #3 Excerpt

In order to evaluate Mr. Jones's lift capacity in a manner that would be safe, reliable and valid, the EPIC Lift Capacity test was utilized. Test results are presented in the table below:

| Test | Range | Frequency | MAW | % tile | RAW | % tile |
|---|---|---|---|---|---|---|
| 1 | Knuckle to Shoulder | 1/cycle | 80 lbs | 70th | .44 | 70th |
| 2 | Floor to Knuckle | 1/cycle | 80 lbs | 45th | .44 | 45th |
| 3 | Floor to Shoulder | 1/cycle | 80 lbs | 65th | .44 | 65th |
| 4 | Knuckle to Shoulder | 4/cycle | 50 lbs | 40th | .28 | 35th |
| 5 | Floor to Knuckle | 4/cycle | 50 lbs | 25th | .28 | 25th |
| 6 | Floor to Shoulder | 4/cycle | 50 lbs | 50th | .28 | 40th |

Mr. Jones's high risk work style was acceptable throughout. He demonstrated excellent body mechanics. His heart rate response to the tasks indicates that he put forth full effort.

As in previous lifting tests, his symptom responses to the tasks consisted of pain in the cervical area which was controlled through simple cervical stretching.

Mr. Jones's maximum acceptable weight exceeds 80 pounds on an occasional basis over a full range of motion. His maximum acceptable weight is 50 pounds on a frequent basis over a full range of motion. This corresponds to work at the "Medium" physical demand characteristics level as dined by the United States Department of Labor and depicted in the chart that is enclosed with this report.

Mr. Jones has improved substantially over the course of the work hardening program. Based on his performance, it appears likely that he will be able to return to his usual and customary employment for a full eight-hour work day.

Note that this evaluation did not take Mr. Jones to his maximum acceptable weight on an occasional basis because the job target for this frequency was 80 pounds. He reported that he was able to lift more weight, rated the RPL at less than eight, and had a good heart rate response at 80 pounds. Even though he was willing to go forward and lift additional weight for Test #1, Test #2, and Test #3, it would have been inappropriate for the evaluator to do so.

Example 3

The safety of a test and the test's stability over time within the evaluee and across evaluators are fundamental requirements. To address these issues, three studies were designed. The purpose of Study #1 was to study the safety and intrarater reliability of the ELC in a sample of healthy subjects in a laboratory setting. The purpose of Study #2 was to study the safety and inter-rater reliability of the ELC test in a sample of subjects who were disabled with musculoskeletal impairment in a laboratory setting. The purpose of Study #3 was to study the safety and intra-rater reliability of the ELC test in a sample of healthy subjects who would be tested by a variety of evaluators in a variety of settings.

For Study #1, healthy active male paid volunteers were recruited. These subjects were active exercisers with no impairment, and no injuries within the prior 12 months. Out of thirty-four (34) volunteers, twenty-seven (27) passed the screening to become subjects in the study. All but one of the subjects who passed the screening eventually completed the study. This subject dropped out due to scheduling problems. For Study #2, male (n=9) and female (n=5) paid volunteers were recruited from the rolls of closed cases at a rehabilitation center. Out of eighteen (18) volunteers, fourteen (14) passed the screening to become subjects in the study. All of these subjects were unemployed due to impairment of the spine (n=8) or lower extremity (n=6) which had resulted in chronic disability. All were medically stable with stable musculoskeletal signs and symptoms and had reported no injuries within the prior 12 months. All completed the study. For Study #3, 318 healthy volunteers (males=142, females=176) were recruited by sixty-five trained evaluators as part of the certification program for the EPIC Lift Capacity test. The evaluators included twenty-five physical therapists, thirteen kinesiologists, eleven occupational therapists, and seven exercise therapists in addition to other health care professionals. For fifty-one of the evaluators, the highest level of academic preparation was a bachelor's degree in various health care fields, while ten evaluators had graduate degrees in health care fields. The remaining four evaluators who received certificates as "evaluation technicians" allowing practice under the supervision of a trained professional, had either two-year college degrees or bachelor's degrees in fields other than health care. Evaluators had various levels of experience in rehabilitation, ranging from two years to twenty years. Average (SD) number of years in rehabilitation practice was 10.2 (6.9) years.

Training of all evaluators was conducted by the inventor or a master's-degreed physical therapist who was specially trained and qualified to be an instructor. Prior to administering the ELC, each evaluator trainee was required to attend a seven-hour training session, pass a written knowledge examination, observe one complete test conducted by the instructor, perform one test under supervision, and observe at least two tests that were performed by others under supervision. Subsequently, to become certified, each evaluator was required to perform ten complete tests on five subjects administered on a test-retest basis. Thirty-three of the evaluators were trained in one large group training session at the Canadian Back Institute (CBI) in Toronto, Ontario, Canada. The remaining 32 had participated in small group training sessions conducted by the Employment and Rehabilitation Institute of California (ERIC). All evaluators were trained during the fourteen-month period from November, 1992 through December, 1993. Evaluators were practicing in seven states in the United States and four Canadian provinces.

All subjects received, reviewed and signed informed consent documents. Subjects in all studies completed a health questionnaire and were screened by interview for cardiac abnormalities or current use of cardiac medications. Subjects were required to have resting blood pressure that did not exceed 159/100 and resting heart rate that did not exceed 90 beats per minute. Subjects received a ten-minute warm-up consisting of a three-minute step-test followed by supervised stretching of the spine and lower extremities immediately prior to ELC testing. The disabled subjects were additionally screened using a procedure to evaluate standing range of motion and walking balance. On the first occasion of testing, all subjects were tested on the ELC using the standard procedures presented in the *ELC Examiner's Manual*. Subjects received a two-minute standing rest between each of the sub-tests. Subjects returned for re-testing 5 days to 17 days after the initial test. After inquiring about symptom responses on the day after the initial test, the same warm-up and test procedures were followed. For the disabled subjects in Study #2, a different evaluator was used to allow inter-rater comparisons. The data for Study #3 were based on records submitted by the evaluator trainees during the certification process. These were reviewed carefully on a structured basis for adherence to the evaluation guidelines. Approximately 4% of the tests that were submitted did not meet these criteria and were not accepted. As an example, more than half of the excluded subjects did not meet heart rate or blood pressure guidelines prior to testing. The exclusions were carefully monitored by the first author and were only based on adherence to the evaluation guidelines without reference to actual test performance.

Characteristics of the subjects for Study #1 and Study #2 are presented in Table 1. Unpaired t-tests demonstrated that healthy subjects have resting heart rates that are lower (p=0.0001) than disabled subjects, probably reflecting a better level of aerobic conditioning although health subjects' age also was lower (p=0.01) than disabled subjects.

TABLE 1

Anthropometric comparison of subjects in Study #1 and Study #2.

| | Study #1 (Healthy) | Study #2 (Disabled) | |
|---|---|---|---|
| | Male (n = 26) | Male (n = 9) | Female (n = 5) |
| Age[a](SD) | 24.8 (2.) | 32.4 (8.0) | 31.0 (6.3) |
| Height[b](SD) | 179.17 (7.5) | 175.52 (6.0) | 165.64 (6.1) |
| Weight[c](SD) | 83.35 (13.1) | 77.32 (8.9) | 60.47 (6.3) |
| Resting HR[d](SD) | 68.85 (11.0) | 75.44 (9.2) | 82.60 (5.0) |

[a]Mean (SD) years.
[b]Mean (SD) centimeters.
[c]Mean (SD) kilograms.
[d]Mean (SD) beats per minute.

Characteristics of the subjects for Study #3 are presented in Table 2. A two factor-analysis of variance based on gender and training site demonstrated a significant difference in terms of age ($F_{1,313}$=4.98, p<0.05). There was no significant difference between the groups in terms of height or weight, although the expected gender differences in these variables were found. Interestingly, resting heart rate demonstrated both a gender difference ($F_{1,313}$=5.98, p<0.01) and a difference attributable to training site ($F_{1,313}$=4.22, p<0.05).

TABLE 2

Anthropometric comparison of subjects across training groups.

| | CBI | | ERIC | |
|---|---|---|---|---|
| | Male (n = 79) | Female (n = 83) | Male (n = 63) | Female (n = 93) |
| Age[a](SD) | 32.94 (9.4) | 31.04 (7.3) | 30.35 (8.2) | 29.48 (8.2) |
| Height[b](SD) | 177.03 (9.3) | 164.95 (8.6) | 177.40 (7.8) | 164.77 (7.2) |
| Weight[c](SD) | 86.18 (15.0) | 61.43 (10.7) | 81.46 (13.7) | 61.79 (10.3) |
| Resting HR[d](SD) | 76.03 (14.4) | 77.02 (12.2) | 71.03 (10.6) | 76.55 (9.1) |

[a]Mean (SD) years.
[b]Mean (SD) centimeters.
[c]Mean (SD) kilograms.
[d]Mean (SD) beats per minute.

In Study #1 and Study #2, none of the subjects terminated any test because of work behavior or inability to complete all task segments. Two of the disabled subjects were not tested with Test #6 because earlier performance on Test #3 was limited to 6.8 kilograms or less. this is because the starting weight for Test #6 is 40% of the maximum achieved on Test #3 (refer to Table 4) and the weight of the empty crate is 4.5 kilograms. Four of the disabled subjects stopped one or more tests in the battery because of heart rate limits, while this occurred with only one healthy subject. The majority of the disabled subjects' tests were terminated by self-perceived report of maximum or achievement of the psychophysical rating maximum, frequently with concordance between these measures. None of the disabled subjects achieved the load guidelines. In contrast, 18 (69%) of the healthy subjects achieved or exceeded the load guidelines. For all but three of these subjects, the load guidelines usually were in concordance with termination based on the psychophysical rating. That is, only three subjects significantly exceeded their load guidelines while rating the psychophysical load at a relatively low level. Maximum acceptable loads achieved for each test with the standard ELC test protocol are presented in Table 3 and in Table 4.

TABLE 3

Comparison of Study #1 healthy male subjects (n = 26) in terms of maximum acceptable weight across all ELC subtests.

| | Test | Retest |
|---|---|---|
| Test #1[a] | 34.62 (7.9) | 35.14 (8.5) |
| Test #2 | 38.81 (7.5) | 38.55 (7.9) |
| Test #3 | 34.88 (8.4) | 34.35 (7.7) |
| Test #4 | 28.00 (6.2) | 28.32 (6.6) |
| Test #5 | 31.03 (7.5) | 31.29 (6.8) |
| Test #6 | 26.40 (6.7) | 27.36 (6.9) |

[a]Mean (SD) kilograms.

TABLE 4

Comparison of Study #2 disabled subjects (n = 14) in terms of maximum acceptable weight across all ELC subtests.

| | Male (n = 9) | | Female (n = 5) | |
|---|---|---|---|---|
| | Test | Retest | Test | Retest |
| Test #1[a] | 15.64 (6.4) | 14.65 (6.7) | 12.73 (5.9) | 11.82 (4.1) |
| Test #2 | 22.18 (6.6) | 18.18 (7.9) | 15.45 (6.9) | 14.55 (8.1) |
| Test #3 | 17.17 (7.1) | 15.15 (7.9) | 12.73 (6.7) | 13.64 (7.2) |
| Test #4 | 11.62 (5.1) | 11.62 (4.6) | 10.00 (5.0) | 10.00 (5.0) |
| Test #5 | 17.17 (5.5) | 16.16 (6.5) | 11.82 (6.1) | 12.73 (5.9) |
| Test #6 | 10.80 (4.2) | 11.36 (4.9)[b] | 10.23 (2.3) | 10.23 (2.3)[b] |

[a]Mean (SD) kilograms.
[b]One case deleted with missing values.

In Study #3, 12 of the male subjects and 15 of the female subjects who were initially tested did not return for the retest session, usually for scheduling reasons. Twelve of the subjects who returned were not tested with all of the frequent tests because each subject's earlier performance on the infrequent tests was limited to 6.8 kilograms or less. Thus, for these subjects, the starting weight for the frequent test was below 4.5 kilograms (refer to Table 4), the weight of the empty container. A two factor-analysis of variance of gender and training site demonstrated a significant difference in terms of maximum acceptable weight based on training site for the first of the six tests in the ELC battery on both the test ($F_{1,313}$=11.88, p<0.001) and the re-test ($F_{1,285}$=4.37, p<0.04), but not on the other tests in the battery. The expected gender differences in maximum acceptable weight were found. These data are presented in Table 5 and Table 6.

TABLE 5

Comparison of male subjects in terms of maximum acceptable weight across all ELC subtests.

| | CBI Test (n - 79) | CBI Retest (n - 73) | ERIC Test (n = 63) | ERIC Retest (n = 57) |
|---|---|---|---|---|
| Test #1[a] | 33.49 (8.8) | 32.88 (9.6) | 30.74 (7.2) | 31.42 (8.1) |
| Test #2 | 36.65 (10.2) | 36.15 (10.2) | 36.40 (7.9) | 36.28 (8.8) |
| Test #3 | 32.76 (9.7) | 32.66 (10.0) | 31.93 (7.0) | 31.90 (7.6) |
| Test #4 | 26.28 (8.3) | 26.77 (8.5) | 25.90 (5.6) | 26.04 (7.0) |
| Test #5 | 28.29 (9.9) | 29.39 (9.9) | 29.69 (6.8) | 29.75 (6.9) |
| Test #6 | 23.77 (8.7) | 25.07 (8.7) | 24.17 (6.6) | 26.64 (6.7) |

[a]Mean (SD) kilograms.

TABLE 6

Comparison of female subjects in terms of maximum acceptable weight across all ELC subtests.

| | CBI Test (n - 82) | CBI Retest (n - 77) | ERIC Test (n = 93) | ERIC Retest (n = 83) |
|---|---|---|---|---|
| Test #1[a] | 20.26 (7.1) | 20.04 (6.9) | 17.64 (4.4) | 17.91 (4.7) |
| Test #2 | 25.17 (8.7) | 25.27 (9.3) | 22.68 (6.4) | 22.98 (7.2) |
| Test #3 | 19.17 (6.7) | 19.21 (6.7) | 17.25 (4.7) | 17.50 (4.7) |
| Test #4 | 16.62 (6.0) | 16.88 (5.9) | 14.48 (4.3) | 14.90 (4.7) |
| Test #5 | 20.51 (8.0) | 20.55 (7.9) | 18.30 (5.6) | 19.11 (6.2) |
| Test #6 | 15.05 (5.5) | 15.97 (5.6) | 13.91 (4.8) | 14.24 (4.6) |

[a]Mean (SD) kilograms.

None of the subjects reported injuries as a consequence of participation in either test session. However. several healthy subjects in Study #1 and Study #3 reported next-day symptoms, typically reported as soreness in the hamstring muscles. These typically resolved with the use of stretching or non-prescription analgesics such as aspirin or Tylenol®. None of the subjects required medical attention. None of the disabled subjects in Study #2 reported new symptoms.

Reliability on a test-retest basis of the maximum acceptable weight achieved by each subject on each sub-test in the ELC battery was evaluated through the use of Pearson product moment correlations for those subjects on whom complete test-retest data sets were available. Because the Pearson r statistic is not sensitive to systematic variation in performance such as might be found in any test requiring some degree of the skill or familiarity, separate intra-class correlations (ICC 1,1) also were calculated for the data from Study #3. If a learning effect were present based on the developing skill of the evaluator during the test-retest process, the ICC would be sensitive to this effect. These data are presented in Table 7.

TABLE 7

Pearson product-moment correlation (r) and intra-class correlation (ICC 1, 1) of test-retest reliability across all ELC subtests. All correlations were significant at p < .001.

|  | Study #1 | | Study #2 | | Study #3 | | |
| --- | --- | --- | --- | --- | --- | --- | --- |
|  | n | r | n | r | n | r | ICC |
| Test #1 | 26 | .90 | 14 | .95 | 290 | .92 | .93 |
| Test #2 | 26 | .92 | 14 | .93 | 289 | .87 | .88 |
| Test #3 | 26 | .92 | 14 | .94 | 290 | .92 | .93 |
| Test #4 | 26 | .86 | 14 | .86 | 285 | .90 | .91 |
| Test #5 | 26 | .88 | 14 | .82 | 283 | .89 | .91 |
| Test #6 | 26 | .92 | 12 | .82[a] | 278 | .89 | .91 |

[a]Two cases deleted with missing values.

The current studies demonstrate acceptable intra-rather reliability and inter-rater reliability within a laboratory setting and in the field. The degree of consistency within subjects and across evaluators in the current studies compares well to previous studies.

Example 4

A research project was designed to evaluate reactivity and sensitivity to change in lift capacity as a result of treatment in a sample of spine-impaired adults. The project used a regimen of back strengthening and general body conditioning exercises without practice in lifting tasks.

Fifty-five subjects (29 females and 26 males) studied in a design which randomly assigned subjects on a single-blind basis to one of two groups. Subjects in this study were lumbar spine patients in the Orthomed program in the Department of Orthopaedics at the University of California San Diego. Subjects reported onset of symptoms 7.1 (SD= 4.6) months prior to program entry. Subjects were diagnosed as suffering degenerative lumbar disc disease (20%), herniated lumbar disc (11%), lumbar strain (25%), or were identified as suffering from low back pain without further diagnostic description (25%). Definitive diagnoses were not available for all subjects. Approximately two-thirds of the subjects were workers compensation claimants. Subject characteristics are presented in Table 1.

TABLE 1

Anthropometric comparison of subjects.

|  | Group One | | Group Two | |
| --- | --- | --- | --- | --- |
|  | (n = 14) | (n = 16) | (n = 12) | (n = 13) |
| Age[a] (SD) | 49.50 (12.7) | 48.94 (11.3) | 46.42 (15.7) | 43.38 (10.2) |
| Height[b] | 178.52 (7.3) | 164.21 (8.3) | 178.64 (5.9) | 166.66 (8.9) |
| Weight[c] | 83.50 (14.2) | 68.46 (12.4) | 88.48 (24.7) | 62.90 (7.5) |

[a]Mean (SD) years.
[b]Mean (SD) centimeters.
[c]Mean (SD) kilograms.

Upon referral to the treatment program, all subjects were provided with an informed consent document and a brief description of the research project. After consent was obtained from the subject, each was randomly assigned to one of two groups, using a coin-flip procedure. All subjects received the same treatment program of eight weeks duration that did not involve lifting practice or use of the EPIC Lift Capacity test (ELC) test apparatus. Subjects in Group One underwent ELC testing before and after treatment, while subjects in Group Two underwent ELC testing only after treatment. In this way, any possible reactivity effects were able to be isolated. Screening, consent, randomization and testing were performed by personnel other than treatment staff. Treatment staff were blind to group assignment. The ECL test was used to evaluate lift capacity in the standard manner but was not used for exercise or for work simulation during the course of treatment. Measures were recorded before and after treatment for isometric back strength, pain ratings, functional self-perception, and activity level. Back strength was evaluated by the MedX® Lumbar Extension machine using standard protocols. Pain was rated on a ten-point visual analog scale using a Million protocol. Self-perception was evaluated by the *Spinal Function Sort*. Activity level was evaluated by the *Oswestry Questionnaire*. All patients participated in the normal treatment sessions on a twice-per-week basis over an eight-week period. Treatment occurred in one 60-minute session and involved the use of the MedX® Lumbar Extension machine and seven variable resistance exercise units, including leg extension, leg flexion, hip extension, hip flexion, latissimus pull-down, seated row, and overhead press. In addition, each patient underwent 10 minutes to 20 minutes of cardiovascular conditioning using a bicycle ergometer, Stairmasters, or exercise treadmill. After eight weeks, on the last day of treatment, ELC testing was performed on all subjects. Two different evaluators were used; one was an exercise physiologist while the other was a physician. Both had been formally trained in the ELC procedures. The same evaluator was used for both pre-test and post-test if the subject was in Group One. Post-treatment measures also were recorded for isometric back strength, pain, selfperception, and activity level.

A series of unpaired t-Tests demonstrated that there were no significant differences within each gender between Group One and Group Two in terms of age, height and weight. A paired t-Test comparing the Group 1 subjects on the ELC tests before treatment and after the treatment program found a significant effect ($t_{29}$=5.47, p=0001). An unpaired t-Test comparing the Group One with the Group Two subjects after the treatment program found no significant difference ($t_{53}$= 0.38, p=0.71). Thus, there appears to be no reactivity effect on subsequent ELC test performance. The mean ELC performances are presented in Table 2.

TABLE 2

Effect of prior ELC test performance in terms of change over the course of treatement.

| Group | Before | After |
|---|---|---|
| Group 1 (n = 30) | 14.00 (6.3)[a] | 16.81 (6.7) |
| Group 2 (n = 25) | na | 16.10 (7.3) |

[a]Mean (SD) years.

A two-factor repeated measure analysis of variance which investigated change in lift capacity on a gender basis found substantial improvement in lift capacity over the course of treatment ($F_{1,28}=28.9$, p=0.0001) for all subjects. Gender was also significant ($F_{1,28}=13.8$, p<0.001). The data for each sex at each time are presented in Table 3.

TABLE 3

Change in lift capacity over the course of treatment.

| Group | Before | After |
|---|---|---|
| Female (n = 16) | 10.66 (3.4)[a] | 13.47 (3.9) |
| Male (n = 14) | 17.80 (6.7) | 20.65 (7.2) |

[a]Mean (SD) kilograms.

There was no interaction effect. Thus, both males and females improved significantly and this improvement was proportional over the course of treatment. A repeated measures analysis of variance which investigated change in lift capacity on an age-group basis found that age was not significant ($F_{2,27}=0.66$, p=0.52), but that there was a significant interaction effect ($F_{2,27}=8.1$, p=0.0017). Older people did not improve lift capacity over the course of treatment. The data for each age group at each time are presented in Table 4.

TABLE 4

Effect of age on change in lift capacity over the course of treatment.

| Group | Age Range | Before | After |
|---|---|---|---|
| Young (n = 16) | 18–40 years | 15.15 (11.5)[a] | 21.67 (11.6) |
| Middle Age (n = 17) | 41–55 years | 12.01 (5.9) | 16.04 (5.9) |
| Mature (n = 8) | 56–70 years | 14.01 (2.3) | 15.43 (2.8) |

[a]Mean (SD) kilograms.

A two-factor repeated measures analysis of variance which compared males and females in terms of the means of all three MedX tests (n=38) found substantial improvement in back strength over the course of treatment ($F_{2,36}=73.81$, p=0.0001). Gender was significant ($F_{1,36}=32.13$, p=0.0001). The data for each sex before and after treatment are presented in Table 5.

TABLE 5

Change in performance on several variables over the course of treatment.

| Test | n | Before | After |
|---|---|---|---|
| Females | | | |
| MedX | 18 | 69.38[a] | 114.88 |
| RPC | 27 | 120.82[b] | 131.89 |
| Pain | 26 | 6.15[c] | 4.92 |
| Oswestry | 25 | 13.92 | 11.80 |
| Males | | | |
| MedX | 20 | 127.05 | 213.22 |
| RPC | 26 | 138.73 | 152.08 |
| Pain | 24 | 5.48 | 3.65 |
| Oswestry | 24 | 11.79 | 9.50 |

A repeated measures analysis of variance which investigated the effect of gender on rating of perceived capacity (RPC) found significant improvement ($_{1,51=}$ 6.72, p=0.01). Gender was nearly significant ($F_{1,51}=3.67$, p=0.061). The data for each sex before and after treatment are presented in Table 5.

A repeated measures analysis of variance which compared pain ratings of males and females found substantial improvement in pain over the course of treatment ($F_{1,48}=31.16$, p=0.0001). Gender was not significant nor was an interaction effect. The data for each sex before and after treatment are presented in Table 5. These data indicate that subjects made improvement in pain over the course of treatment and that there were no significant differences in terms of either the initial score, exit score, or degree of improvement between males and females.

A two-factor repeated measures analysis of variance which compared male and female subjects in terms of initial Oswestry score and exit Oswestry score found significant improvement over the course of treatment ($F_{1,48}=12.35$, p=0.001). Gender was not significant and there was not a significant interaction effect. The data for each age group before and after treatment are presented in Table 5. These data indicate that improvement was found in the Oswestry score over the course of treatment and that there is no significant difference between males aneachmales at each time of testing, nor is there a significant difference in terms of their response to treatment.

The results of the current study demonstrate that reactivity to the ELC was too low to be measured within the context of this treatment program, at least when used at the start of a treatment program and not used during the program as an exercise or work simulation task. While reactivity may exist with this test in other applications, within the paradigm utilized here, it was not detectable. Thus, changes in test performance over the course of treatment are likely to reflect the change in the underlying capacity of the patient.

All publications and patent applications mentioned in this specification are indicative of the level of skill of those skilled in the art to which this invention pertains. All publications and patent applications are herein incorporated by reference to the same extent as if each individual publication or patent application was specifically incorporated by reference.

Although the present invention has been described above in terms of a specific embodiment it is anticipated that alterations and modifications thereof will no doubt become apparent to those skilled in the art. It is therefore intended that the following claims be interpreted as covering all such alterations and modifications as fall within the true spirit and scope of this invention.

What is claimed is:

1. A method for evaluating lifting work capacity of a person, said method comprising the steps of:
   (a) determining a maximum acceptable weight that said person can lift in a test comprising the steps of:
      (1) selecting a starting weight a maximum allowable heart rate and a starting heart rate for said person;
      (2) constantly monitoring a heart rate of said person during said test;
      (3) requiring said person to lift a weight from a series of weights beginning with said starting weight;
      (4) monitoring said heart rate of said person during lifting of said weight and if said heart rate exceeds said maximum allowable heart rate while said person is lifting said weight, stopping said test;
      (5) monitoring said heart rate of said person after lifting said weight and if said heart rate does not return to said starting heart rate within a predetermined period of time in the range of 30 to 120 seconds after said person has lifted said weight, stopping said test; and
      (6) if said test is not stopped repeating steps (3)–(5) until said test is stopped in steps (4) or (5) and, in step (3), requiring said person to lift a next weight in said series of weights where said next weight in said series of weights is heavier than the previous weight in said series of weights that was previously lifted by said person in step (3),
   whereby said maximum acceptable weight is the heaviest weight of said series of weights that said person can lift before said heart rate of said person during lifting exceeds said maximum allowable heart rate or said heart rate of said person after lifting does not return to said predetermined starting heart rate within said predetermined period of time; and
   (b) obtaining a normative performance ranking by locating said maximum acceptable weight on a table of normative data and locating a corresponding normative performance ranking,
   whereby said lifting work capacity of said person is obtained.

2. The method of claim 1, further comprising the step of selecting a lifting limit.

3. The method of claim 2 wherein said maximum acceptable weight does not exceed said lifting limit.

4. The method of claim 2 wherein said lifting limit is the lesser of a target weight or a maximum lifting weight.

5. The method of claim 4 wherein said maximum lifting weight is based on said person's height.

6. The method of claim 4 wherein said maximum lifting weight is gender-specific.

7. The method of claim 1, wherein said normative performance ranking is a percentile value based on maximum acceptable weight.

8. The method of claim 1, wherein said normative performance ranking is a percentile value based on the maximum acceptable weight and the body weight of said person.

9. The method of claim 1, further comprising the step of determining said person's rating of a perceived load which is said person's judgment as to the weight said person lifted.

10. The method of claim 9 wherein said step of determining said person's rating of a perceived load is accomplished by said person selecting said perceived load from a list of standard perceptions.

11. The method of claim 1, further comprising the step of monitoring said person's pain indicators.

12. The method of claim 1, further comprising the step of monitoring said person's body mechanics.

13. The method of claim 1, wherein said person dies not know the quantity of weight to be lifted.

14. The method of claim 1 wherein said starting heart rate is calculated by subtracting the age of said person from 220 and then calculating 70% of that value.

15. The method of claim 1, further comprising a step of evaluating high risk work factors during said test to determine said maximum acceptable weight, said step comprising observing the posture of a person, while said person is performing a method for evaluating lifting work capacity of said person, by monitoring said person's stance and any horizontal displacement between said person's spine and a center of gravity of said weight being lifted by said person, determining if said person is exhibiting high risk work factors by comparing said person's stance and said displacement to a table of normative data, and stopping said test if said person exhibits high risk work factors during two consecutive lifts of said weights.

16. A method for evaluating a vertical range lift capacity of a person, said method comprising:
   (a) a first subtest in which a first maximum acceptable weight that said person can lift through a predetermined first vertical range is determined, comprising the steps of:
      (1) selecting a starting weight, a maximum allowable heart rate and a starting heart rate for said person;
      (2) constantly monitoring a heart rate of said person during said subtest;
      (3) requiring said person to lift a weight from a series of weights beginning with said starting weight through a predetermined vertical range;
      (4) monitoring said heart rate of said person during lifting of said weight and if said heart rate exceeds said maximum allowable heart rate while said person is lifting said weight, stopping said test;
      (5) monitoring said heart rate of said person after lifting said weight and if said heart rate does not return to said starting heart rate within a predetermined period of time in the range of 30 to 120 seconds after said person has lifted said weight, stopping said test; and
      (6) if said test is not stopped, repeating steps (3)–(5) until said test is stopped in steps (4) or (5) and, in step (3), requiring said person to lift a next weight is said series of weights where said next weight in said series of weights is heavier than the previous weight in said series of weights that was previously lifted by said person in step (3),
   whereby said first maximum acceptable weight is the heaviest weight that said person can lift before said heart rate of said person during lifting exceeds said maximum allowable heart rate or said heart rate of said person after lifting does not return to said starting heart rate within said predetermined period of time;
   (b) performing at least one subsequent progressive subtest; and
   (c) for each subsequent subtest, determining a corresponding subsequent maximum acceptable weight that said person can lift through a predetermined subsequent vertical range wherein said subsequent vertical range is different for each subtest and said subsequent maximum acceptable weight for each subtest is the heaviest weight that said person can lift before said heart rate of said person during lifting exceeds said maximum allowable heart rate or said heart rate of said person after lifting does not return to said starting heart rate within said predetermined period of time;
   whereby said vertical range lift capacity of said person is evaluated by comparing said subsequent maximum acceptable weights with said first maximum acceptable weight.

17. The method of claim 16 wherein said method is recursive.

18. The method of claim 16 wherein each of said subtests is selected from a sequential series of subtests comprising (a) one lift from knuckle to shoulder level, (b) one lift from floor to knuckle level, (c) one lift from floor to shoulder level, (d) four lifts from knuckle to shoulder level, (e) four lifts from floor to knuckle level, and (f) four lifts from floor to shoulder level.

19. The method of claim 18 wherein each of said subsequent progressive subtests is selected in order from said series.

20. The method of claim 18 wherein each progressive subtest having four repetitions has a preselected starting weight of approximately 40% of the maximum lifted weight of each corresponding one repetition subtest.

21. The method of claim 18 wherein the subtest having one repetition of lifting from floor to shoulder level has a preselected starting weight of approximately 70% of the lesser of the maximum lifted weight of the progressive subtest having one repetition of lifting from knuckle to shoulder level and the progressive subtest having one repetition of lifting from floor to knuckle level.

22. A method for evaluating the constant work capacity of a person, said method comprising the steps of:

(a) determining a maximal frequency for said person in a test comprising the steps of:
  (1) selecting a weight and a maximum allowable heart rate,
  (2) constantly monitoring a heart rate of said person during said test,
  (3) requiring said person to repeatedly lift said weight through a predetermined vertical range at a maximal frequency for said person; and
  (4) monitoring said heart rate of said person during lifting and if said heart rate exceeds said maximum allowable heart rate while said person is lifting said weight, stopping said test,
whereby said maximal frequency is the number of lifting cycles said person completes before said heart rate of said person exceeds said maximum allowable heart rate; and (b) obtaining a performance ranking by locating said maximal frequency on a table of normative data and locating a corresponding performance ranking,
whereby said constant work capacity of said person is obtained.

23. The method of claim 22 wherein said performance ranking is a Method-Time-Measurement percentage.

\* \* \* \* \*